United States Patent [19]

Moon

[11] Patent Number: 4,534,897

[45] Date of Patent: Aug. 13, 1985

[54] PIPERAZINONE, PIPERAZINE, 1,4-DIAZEPIN-2-ONE AND 1,4-DIAZEPINE INTERMEDIATE COMPOUNDS

[75] Inventor: Malcolm W. Moon, Kalamazoo, Mich.

[73] Assignee: The Upjohn Company, Kalamazoo, Mich.

[21] Appl. No.: 598,608

[22] Filed: Apr. 10, 1984

Related U.S. Application Data

[62] Division of Ser. No. 153,435, May 27, 1980.

[51] Int. Cl.$^3$ .......................................... C07D 210/00
[52] U.S. Cl. ............................. 260/239.3 R; 544/373; 544/384; 544/388; 544/399; 548/228; 260/239 BC
[58] Field of Search ...................... 260/239.3 R, 112.5, 260/239 BC; 544/384, 373, 388, 399

[56] References Cited

U.S. PATENT DOCUMENTS 4,251,438 2/1981 Moon ........................... 260/112.5 R

OTHER PUBLICATIONS

Nature, 258, 577–579, (1975), vol. 258, Hughes et al.
Can. J. Chem. 48, 163–175, (1970), Genik-Sas-Berezowsky et al.
J. Chem. Soc. (C), 2390, (1971).
Bulletin of Chem. Soc. Jap. 46, 844–851, (1973), Mashihara, Misao et al.
Bull. Chem. Soc. Jap. 46, 3612–3613, (1973), Uchida, H. et al.

*Primary Examiner*—Donald G. Daus
*Assistant Examiner*—S. A. Gibson
*Attorney, Agent, or Firm*—Bruce Stein

[57] ABSTRACT

The compounds of the following formulas

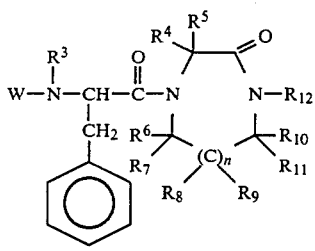

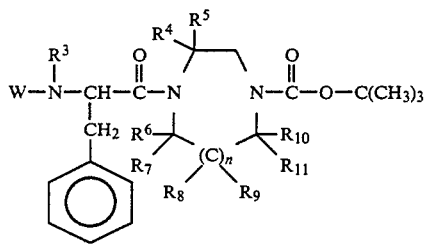

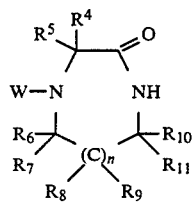

where W is hydrogen, benzyloxycarbonyl, or t-butoxycarbonyl useful as intermediates for preparing piperazine, piperazinone, 1,4-diazepine and 1,4-diazepin-2-one polypeptide compound.

36 Claims, No Drawings

PIPERAZINONE, PIPERAZINE, 1,4-DIAZEPIN-2-ONE AND 1,4-DIAZEPINE INTERMEDIATE COMPOUNDS

This patent application is a divisional of co-pending patent application Ser. No. 153,435, filed May 27, 1980.

BACKGROUND OF THE INVENTION

Very few drugs are known which are effective mild analgesics. Aspirin and related salicylates are known to relieve mild to moderate pain. However, the salicylates are known to possess a number of very undesirable side effects such as nausea, vomiting, epigastric distress, gastric ulceration and even hemorrhaging. Arthritis patients who are on high doses of salicylate analgesics have reported peptic ulcer symptoms and gastritis. Aspirin is also one of the leading accidental poisoners of children.

Acetaminophen is sold widely for treating mild pain. Acetaminophen is useful in patients who for whatever reason cannot tolerate salicylates. However, some are sensitive to acetaminophen and it is apparently exhibits hepatotoxicity.

The primary drugs available for alleviating severe pain such as pain from fractures, surgery, cancer, back, kidney stones, etc. were the narcotics including both the naturally occurring and synthetic ones. These include morphine, meperidine, codeine, methadone, levorphanol, oxycodone, hydromorphone, and alphaprodine. These narcotic analgesics have the distinct and severe disadvantage of causing physical dependence (addiction), sedation, constipation, nausea, etc.

The more important anti-anxiety agents on the market are benzodiazepines primarily diazepam, chlordiazepoxide, oxazepam and clorazepate. While these agents are of value they can produce drowsiness, fatigue, ataxia and other side effects. The anti-psychotic agents such as chlorpromazine are useful but have undesirable side effects especially drowsiness, jaundice and agranulocytosis.

Hence, there is a definite need to have both better mild, moderate and strong analgesic agents as well as better psychotherapeutic agents. The present invention helps fill these needs.

In 1975 J. Hughes et al. reported in Nature 258, 577 (1975) the opiate-like analgesic activity of 2 pentapeptides:

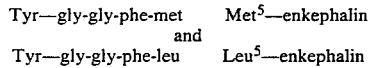

Tyr—gly-gly-phe-met   Met[5]—enkephalin
and
Tyr—gly-gly-phe-leu   Leu[5]—enkephalin Since that time a number of enkephalin-like pentapeptides have been synthesized which are more stable and have high analgesic activity. Generally, these pentapeptides are ones in which the second amino acid (glycine) and/or the fifth amino acid (methionine or leucine) have been modified. Modification of the first, third or fourth amino acid generally leads to an inactive peptide. See, R. C. A. Frederickson, Life Sciences 21, 23 (1977); C. R. Beddell et al., Proc. R. Soc. Lond 198, 249 (1977); A. S. Cutta et al., Life Sciences 21, 559 (1977); D. Roemer et al., Nature 268, 547 (1977) and B. vonBraffenried et al., Nature 272, 729 (1978).

Various substituted piperazinones are known, see R. M. Genck-Sas-Berekowsky and I. H. Spinner, Can. J. Chem. 48, 163 (1970); D. B. Haydock and T. P. C. Mulholland, J. Chem. Soc. (C) 2390 (1971); M. Mashehan et al., Bull. Chem. Soc. Jap. 46, 844 (1978) and H. Vihida and M. Ohta, ibid 46, 3612 (1973). However, none of those compounds are known to possess analgesic or psychotherapeutic activity.

BRIEF DESCRIPTION OF THE INVENTION

Disclosed are polypeptide piperazinones (XII, XXXIV and XXXIX) and polypeptide piperazines (XLV) which are useful as analgesic and psychotherapeutic agents. These compounds are produced by the processes of Charts A1-A3, B1-B4, C, D1-D4, E and F1-F2. The processes of the present invention as disclosed by the Charts to produce the biologically active polypeptides XII, XXXIV, XXXIX and XLV proceed thru a number of novel compounds including compounds of the formula (IX, X, XVII, XXII, XXIII, XXXI, XXXII, XXXIII, XXXVII and XLIV). Therefore, these intermediates are useful to produce the biologically active polypeptides of the present invention.

DETAILED DESCRIPTION OF THE INVENTION

The present invention includes piperazinone and piperazine polypeptides which are useful as analgesics and psychotherapeutic agents.

There are a number of ways of producing the analgesic piperazinone and piperazine polypeptides of the present invention.

Chart A1

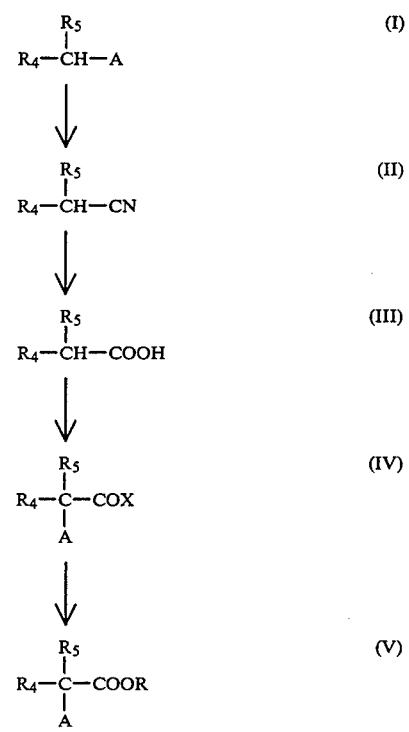

Chart A2

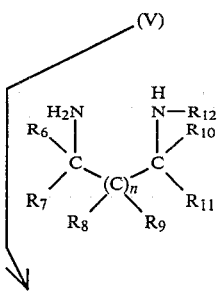
(V)

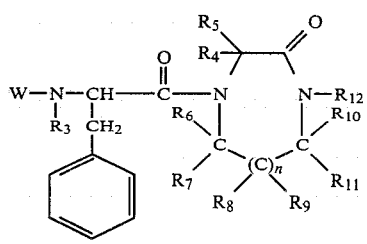
(VI)

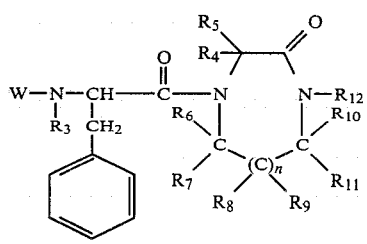
(IX)

-continued
Chart A2

Chart A3

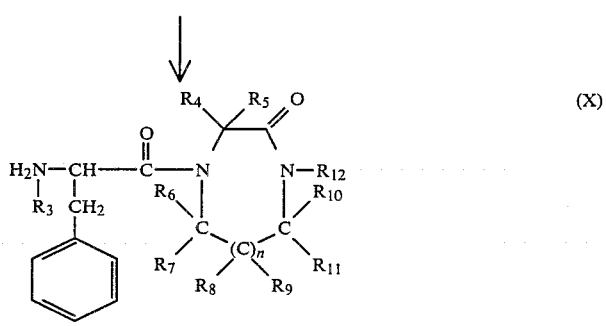
(X)

(1) Protected tripeptide (XI)
(2) Remove protecting group

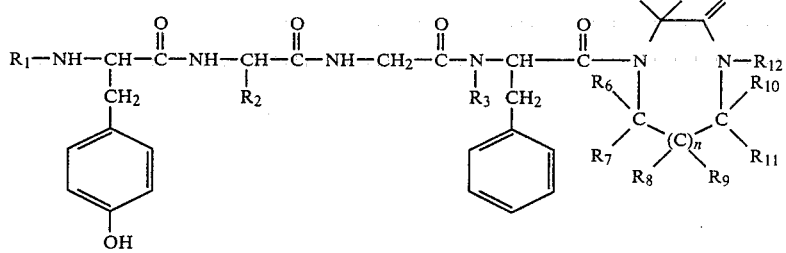
(XII)

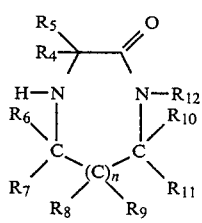
(VII)

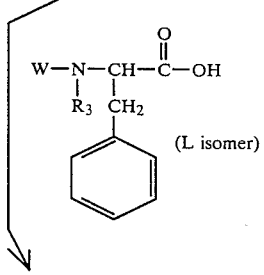
(VIII)

(L isomer)

Charts A1 thru A3 disclose a general method to produce substituted ($R_4$ and $R_5$ are not both hydrogen) piperazinones (XII) where the substituents are added prior to piperazinone ring formation. The compounds of the formula (XII) are truly piperazinones when n is 0 and are hexahydro-2H-1,4-diazepin-2-ones when n is 1, however, for simplicity both series of compounds (n is 0 and 1) will be referred to as "piperazinones". The appropriate alkyl halide (I) is reacted with cyanide in the usual manner to produce the corresponding nitrile (II). $R_4$ is a hydrogen atom, alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}S\text{-}R_{4b}$ or amino substituted alkyl where the alkyl portion is 2 thru 5 carbon atoms. In the cases where $R_4$ is hydroxyalkyl or aminoalkyl, the hydroxy or amine function must be suitably protected during the reaction sequence. Examples of suitable protecting group are benzoyl for hydroxyl and phthalimido for amino. It is preferred that $R_4$ is iso-butyl or $CH_3$—S—$CH_2CH_2$— which would make the cyclic compound (VII) corresponding to the amino acid leucine or methionine respectively. $R_5$ is a hydrogen atom, alkyl of 1 thru 4 carbon atoms, cycloalkyl of 3 thru 5 carbon atoms, cycloalkyl substituted alkyl of 4 thru 7 carbon atoms total. It is preferred that $R_5$ is a hydrogen atom or methyl group. It is more preferred that $R_5$ is a hydrogen atom. A is a chlorine or bromine atom. It is preferred that A is a bromine atom. The nitrile (II) is readily converted by known means to the corresponding acid (III). The acid (III) is then converted to the corresponding α-halo acid halide (IV) by reaction with agents such as thionyl chloride-bromine, bromine-phosphorus, bromine-phosphorus trichloride and thionyl chloride-chlorine. X is a chlorine or bromine atom.

The α-halo acid halide (IV) is reacted with an alcohol to produce the α-halo ester (V). R is a primary or secondary alkyl group of 1 thru 6 carbon atoms, phenyl or cyclohexyl. It is preferred that R is methyl. The α-halo ester (V) is then reacted with the appropriately substituted diamine (VI) which produces the desired piperazinone (VII). In the diamine $R_6$, $R_7$, $R_8$, $R_9$, $R_{10}$, $R_{11}$ and $R_{12}$ are when present independently a hydrogen atom, alkyl of 1 thru 4 carbon atoms, cycloalkyl of 3 thru 5 carbon atoms, cycloalkyl substituted alkyl of 4 thru 7 carbon atoms total with the proviso that the total number of carbon atoms in all these groups together when present is 0 thru 10. n is 0 or 1; it is preferred that n is 0. Alternatively, the piperazinone (VII) can be readily prepared directly from the α-halo acid halide (IV) by reaction with the diamine (VI), see Example 83. The piperazinones (VII) where $R_{12}$ is not a hydrogen atom can be prepared by the process of Charts A1 and A2 using an appropriately substituted diamine (VI). This process will give mixtures because either end of the diamine (VI) can initially react with the α-halo atom of the ester (V). Alternatively, one can start with a piperazinone (XVII) where $R_{12}$ is a hydrogen atom, add the desired $R_{12}$ group (e.g., methyl, Examples 45–48) and then remove the blocking group W' to obtain a piperazinone (VII) where $R_{12}$ is not a hydrogen atom.

This piperazinone (VII) must now be reacted to add the desired polypeptide to the amino-nitrogen to produce the piperazinone polypeptide (XII). First, the piperazinone (VII) is reacted with N-protected-L-phenylalanine (VIII) to produce the N-protected phenylalanylpiperazinone (IX). The N-protected phenylalanylpiperazinone (IX) can be isolated if desired. However, it is preferable to transform it to the phenylalanylpiperazinone (X) without isolating it. When the N-protected L-phenylalanine is reacted with a piperazinone in which $R_4$ is not the same as $R_5$ (VII; D,L- mixture), two diastereoisomers are produced, L,L- and L,D-. These can be separated by means well known to those skilled in the art.

The α-amino group of the phenylalanine is protected (W) either with benzyloxycarbonyl or with t-butoxycarbonyl to prevent polymerization of the phenylalanine reactant. Following formation of the N-protected-phenylalanylpiperazinone (IX) the protecting group is removed, for example by (1) hydrogenation in the presence of an appropriate catalyst such as palladium on carbon, hydrogen bromide in acetic acid particularly in the case where W is benzyloxycarbonyl or (2) reaction with a strong acid such as hydrogen fluoride or trifluoroacetic acid (particularly in the case where W is t-butoxycarbonyl) to produce the phenylalanylpiperazinone (X). The phenylalaninepiperazinone (X) is then reacted with a N-protected tripeptide (XI) to produce the N-protected product. The N-protected product is isolated, purified and reacted with a strong acid such as hydrogen fluoride or trifluoroacetic acid to remove the N-protecting group and give the polypeptidepiperazinone (XII). The N-protected tripeptide is from the amino portion tyrosine, D-alanine and glycine or substituted analogs thereof as defined by $R_1$ and $R_2$. $R_1$ is a hydrogen atom, methyl group or L-arginyl. It is preferred that $R_1$ is a hydrogen atom or L-arginyl. It is more preferred that $R_1$ is a hydrogen atom. $R_2$ is a hydrogen atom, alkyl of 1 thru 3 carbon atoms, hydroxyalkyl where the alkyl portion is 1 thru 3 carbon atoms or $R_{2a}$—S—$R_{2b}$— with the proviso that when $R_2$ is not a hydrogen atom the carbon atom to which $R_2$ is attached is of the D configuration. $R_{2a}$ is alkyl of 1 thru 3 carbon atoms. $R_{2b}$ is alkyl of 1 thru 3 carbon atoms. The N-protected tripeptide (XI) where W is the N-protecting group can be represented as

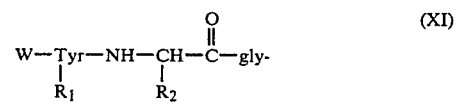

When $R_2$ is a hydrogen atom the above can be represented

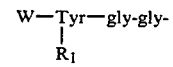

When $R_2$ is a methyl group, the tripeptide (XI) can be represented

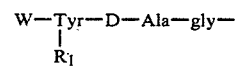

Hence, the polypeptide-piperazinone (XI) where $R_2$ is methyl but without the various substituents can be represented as

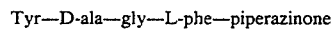

When $R_4$ is 2-methylpropyl, this group taken together with the attached carbon atom and adjacent carbonyl and tertiary amino group is leucine cyclized in the piperazinone ring. Therefore, a further representation (when $R_4$ is 2-methylpropyl, $R_2$ is methyl, and $R_1$ and $R_3$ are hydrogen atoms) of the polypeptide-piperazinone (XII) is

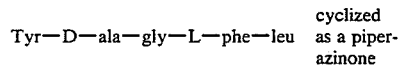

When $R_4$ is $CH_3$—S—$CH_2CH_2$— this group taken together with the attached carbon atom and the adjacent carbonyl and tertiary amino group is methionine cyclized in the piperazinone ring. Therefore, a further representation (when $R_4$ is $CH_3$—S—$CH_2CH_2$—, $R_2$ is methyl and $R_1$ and $R_3$ are hydrogen atoms) of the polypeptide piperazinone (XII) is

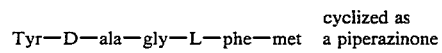

When $R_1$, $R_3$ and $R_4$ are as above but $R_2$ is a hydrogen atom the polypeptide piperazinone (XII) can be represented as Tyr—gly—gly—L—phe—leu  cyclized as a piperazinone and Tyr—gly—gly—L—phe—met  cyclized as a piperazinone Therefore, the polypeptide piperazinone (XII) has a peptide chain containing 4 amino acids connected to a piperazinone ring containing a fifth amino acid cyclized into the piperazinone ring.

Chart A1-A3 disclosed a process to produce piperazinones where the substituents ($R_4$ and/or $R_5$) if present are introduced prior to piperazinone ring formation. Charts B1-B4 disclose a process to produce substituted ($R_4$ and $R_5$ are not both hydrogen) piperazinones where the substituents ($R'_4$ and/or $R'_5$) are introduced after piperazinone ring formation. The 3-unsubstituted piperazinone (XIII) is prepared by reacting ethyl chloroacetate with an N,N'-dibenzylethylenediamine (n=0) or N,N'-dibenzylpropylenediamine (n=1) to form the unsubstituted 1,4-dibenzylpiperazinone (XIII). The 4-benzyl group is removed by hydrogenation using palladium on carbon to give the 3-unsubstituted-1-benzylpiperazinone (XIV). The 4-nitrogen is then protected with the amino protecting group W', where W' is W or benzyl to produce the blocked 3-unsubstituted-1-benzylpiperazinone (XV) which is then alkylated to produce the protected alkylated piperazinone (XVI). $R'_4$ is alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms. It is preferred that $R'_4$ is iso-butyl or $CH_3S$—$CH_2CH_2$—. Next the benzyl group is removed to give (XVII) and then the amino protecting group W' is removed to give the alkylated piperazinone (VIIA). It should be noted that the alkylated piperazinone (VIIA) is within the scope of, and a special case of the piperazinone (VII) where $R_4$ is not a hydrogen atom and $R_5$ and $R_{12}$ are hydrogen atoms.

The alkylated piperazinone (VIIA) could be prepared by the process of Charts A1 and A2, the process of Charts B1 and B2 is an alternative process, and is the preferred process when $R_4$ is alkylthioalkyl.

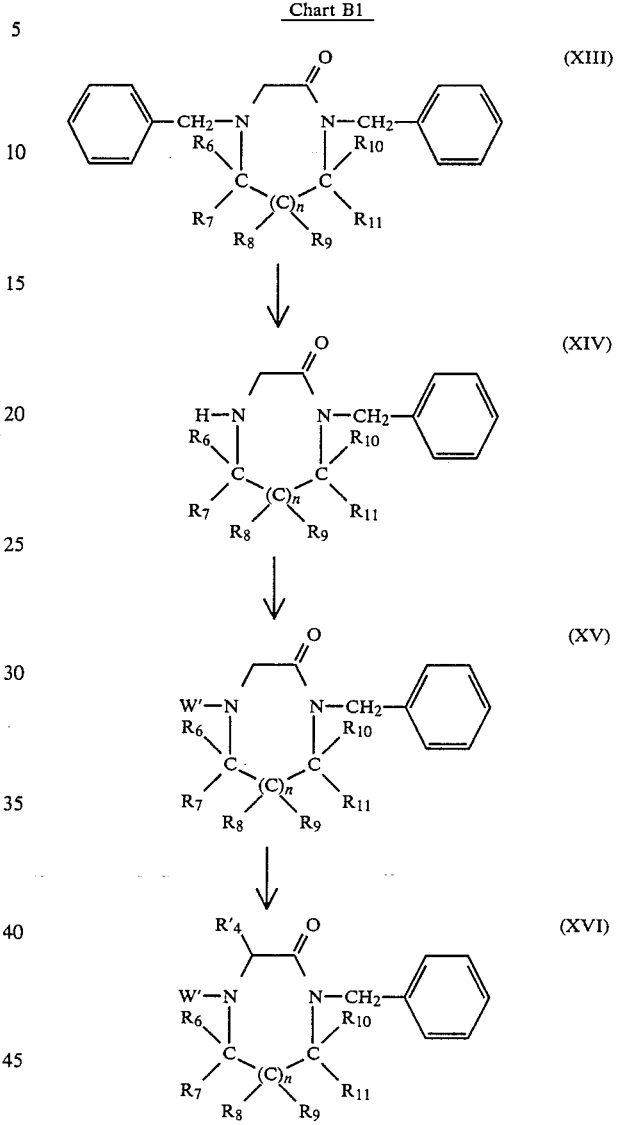

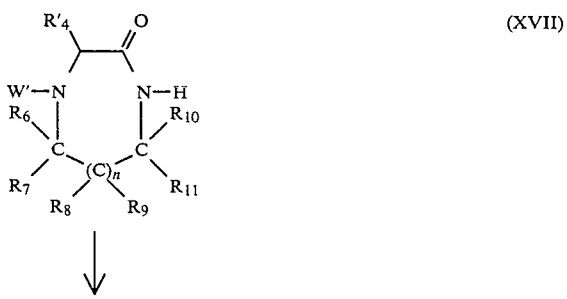

Chart B2
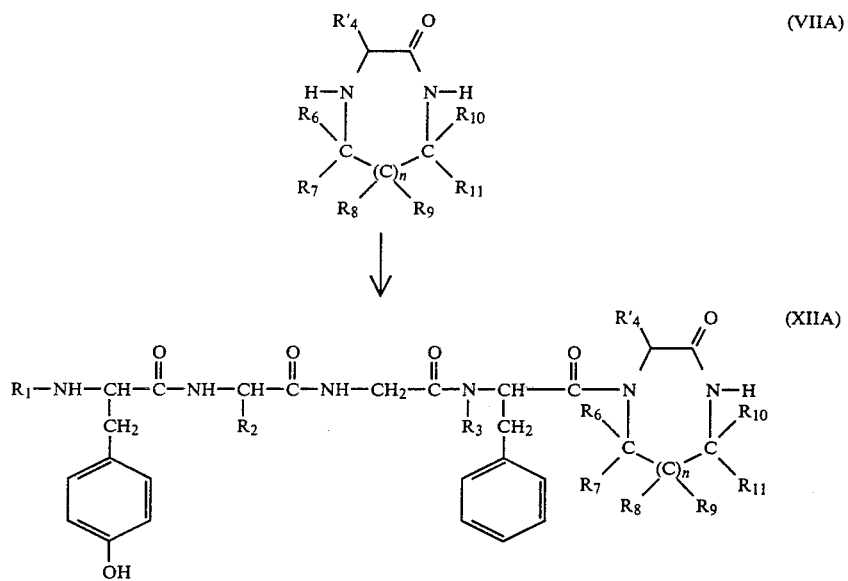
Chart B3
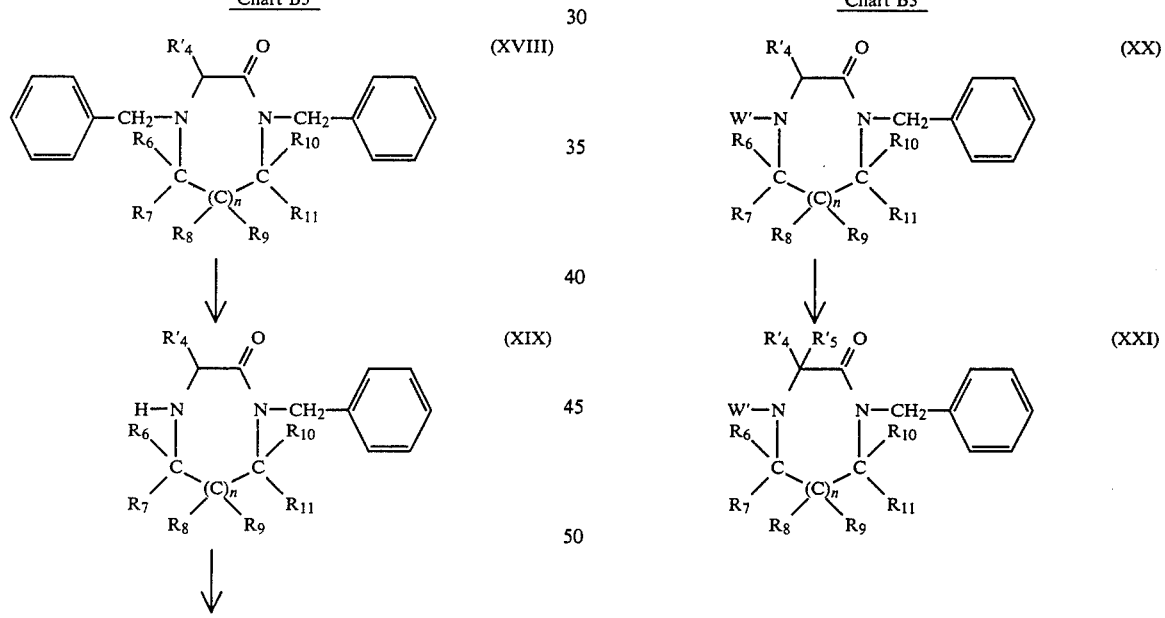
Chart B4
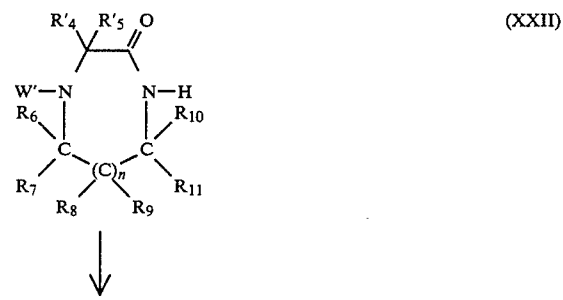

Chart B4

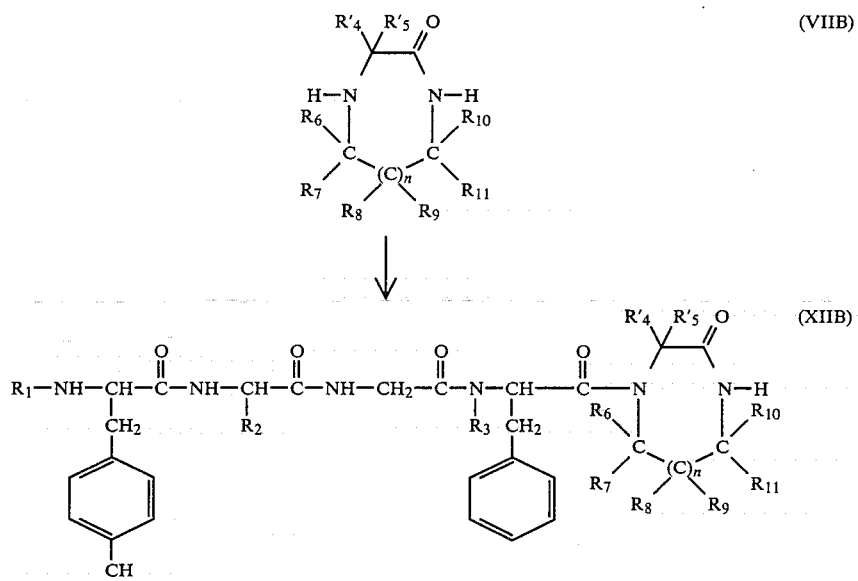

Charts B1 and B2 disclose a process to produce an alkylated piperazinone (VIIA) by introduction of the alkyl group ($R_4'$) after piperazinone ring formation in the special case where $R_{12}$ is a hydrogen atom. A process of preparing an alkylated piperazinone (VIIA), where $R_{12}$ is not a hydrogen atom and where the alkyl group ($R_4'$) is introduced after piperazinone ring formation would involve beginning with 4-benzylpiperazinone, alkylating the nitrogen at the 1-position with a reagent such as methyl iodide (Example 46), to produce the 4-benzyl-1-methylpiperazinone (Example 47) and removal of the protecting benzyl group (Example 48).

The alkylated piperazinone (VIIA) is transformed to polypeptide piperazinone (XIIA) in the same manner as was the piperazinone (VII) was transformed to the polypeptide piperazinone (XII). The polypeptide piperazinone (XIIA) is within the scope and special case of the polypeptide piperazinone (XII) where $R_4$ is not a hydrogen atom and $R_5$ and $R_{12}$ are hydrogen atoms.

The process of Charts B1 and B2 produce an alkylated piperazinone (VIIA) where $R_4$ is not a hydrogen atom. If a dialkylated piperazinone (VIIB) is desired the process of Charts B3 and B4 is followed. The 3-monosubstituted-1,4-dibenzylpiperazinone (XVIII) is either produced directly (Example 49) or by the process of Chart B1, the compound of formula (XVI) where W' is benzyl. The 3-monosubstituted-1,4-dibenzylpiperazinone (XVIII) is reacted in virtually the same manner according to Charts B3 and B4 as the 3-unsubstituted-1,4-dibenzylpiperazinone (XIII) was reacted according to Charts B1 and B2. The dialkylated piperazinone (VIIB) obtained is within the scope of, and a special case of the piperazinone (VII) where $R_4$ and $R_5$ are not hydrogen atoms and $R_{12}$ is a hydrogen atom. $R'_5$ is alkyl of 1 thru 4 carbon atoms, cycloalkyl of 3 thru 5 carbon atoms, cycloalkyl substituted alkyl of 4 thru 7 carbon atoms total with the proviso that the total number of carbon atoms of $R'_5$ and $R_6$–$R_{12}$ together when present is 1 thru 10. The dialkylated piperazinone (VIIB) could be prepared by the process of Charts A1 and A2; the process of Charts B3 and B4 is an alternate process.

The dialkylated piperazinone (VIIB) is transformed to the polypeptide piperazinone (XIIB) in the same manner as the piperazinones (VII and VIIA) were transformed to the polypeptide piperazinones (XII and XIIA). The polypeptide piperazinone (XIIB) is within the scope and a special case of the polypeptide piperazinone (XII) where $R_4$ and $R_5$ are not hydrogen atoms and $R_{12}$ is a hydrogen atom.

Chart C discloses the preferred process for the transformation of hindered or disubstituted ($R_4$ and $R_5$ are both not hydrogen) piperazinone (VIIB) to the phenylalanyl-piperazinone (X). Charts A2 and A3 disclosed the general process for the addition of phenylalanine to a piperazinone (VII) to form the phenylalanine piperazinone (X). That general process is suitable when $R_4$ and $R_5$ are both hydrogen (Examples 10 and 17) or where $R_5$ is hydrogen (Examples 5, 6, 11–16 and 82). However, with the hindered or disubstituted piperazinone (VIIB) the process of Chart C is preferred (Examples 57, 58, 59, 84 and 85).

Charts D1–D4 disclose a process to produce polypeptide piperazinones with a benzyl group substituted in the piperazinone ring α to the carbonyl (attached to the carbon atom between the carbonyl and the non-amide nitrogen atom). The significance of this will be discussed later.

Chart C

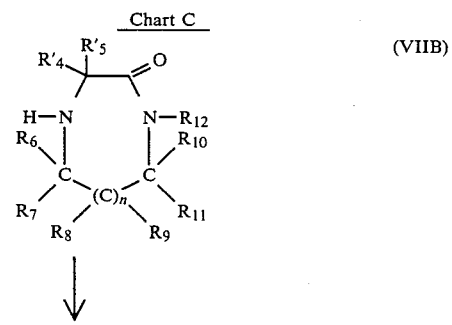

-continued
Chart C
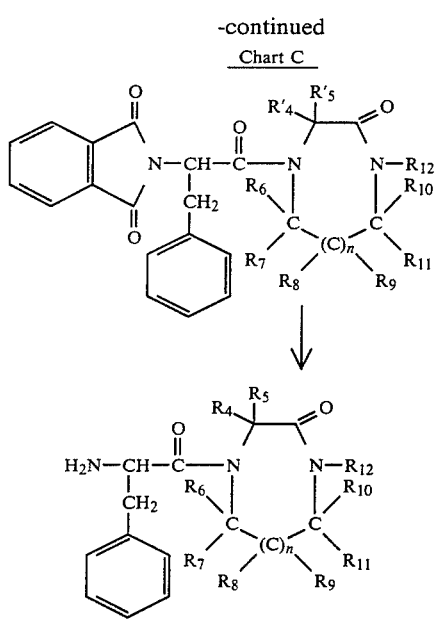
(XXIII)
(X)
Chart D1
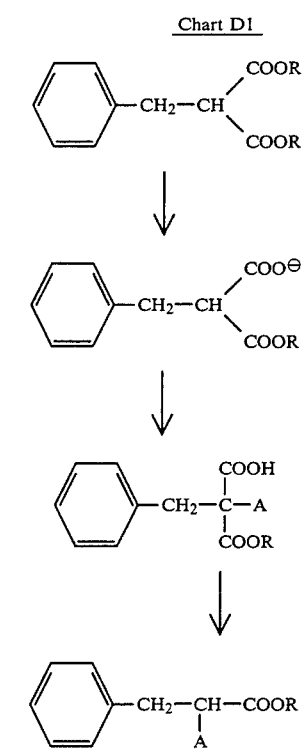
(XXIV)
(XXV)
(XXVI)
(XXVII)
Chart D2
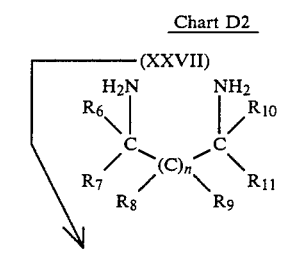
(XXVIII)
-continued
Chart D2
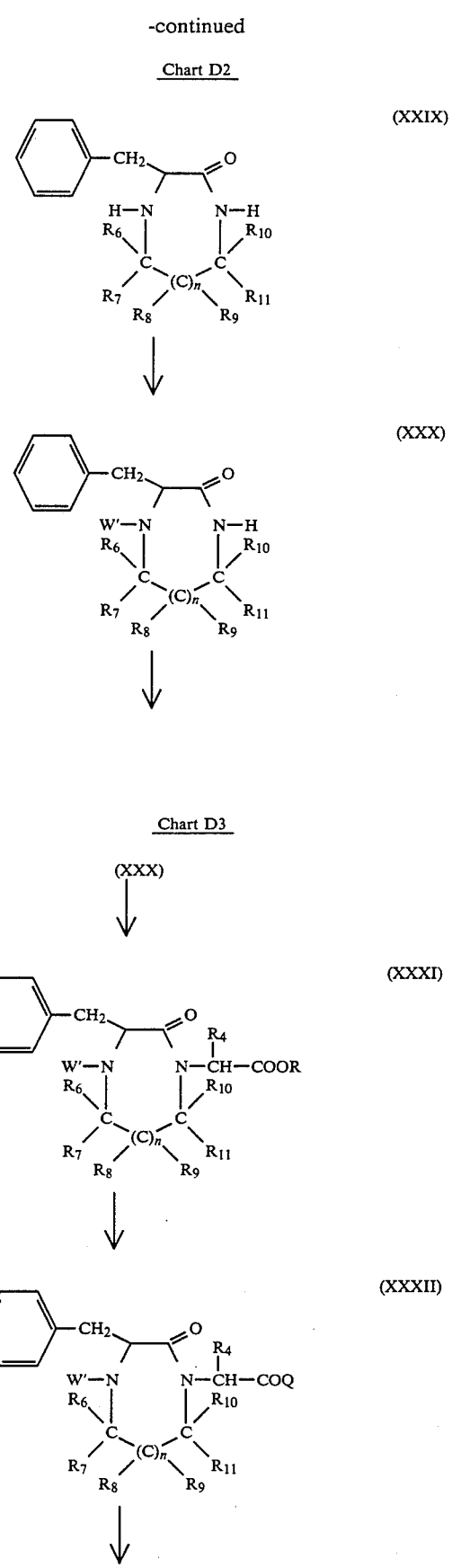
(XXIX)
(XXX)
Chart D3
(XXX)
(XXXI)
(XXXII)

-continued
Chart D3

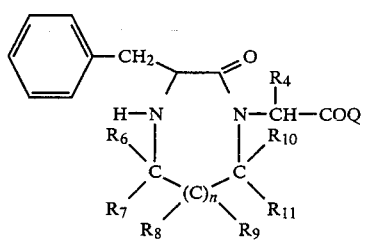
(XXXIII)

Chart D4

(XXXIII)

(1) Protected tripeptide (XI)
(2) Remove protecting group

↓

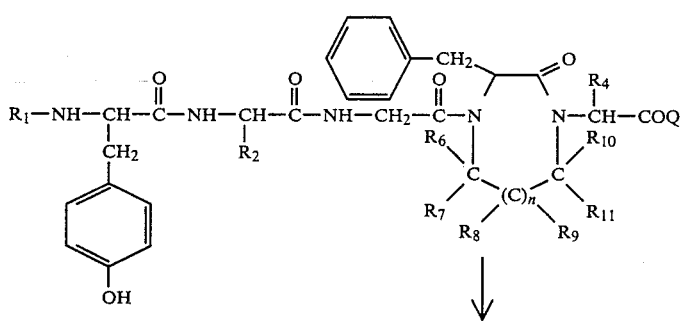
(XXXIV)

↓

The benzyl polypeptide piperazinones (XXXIV) are prepared by transforming the diester (XXIV) to its corresponding monoester salt (XXV) and then to the α-halo acid-ester (XXVI). The α-halo acid-ester (XXVI) is decarboxylated to the benzyl α-halo ester (XXVII) which is similar to the α-halo ester (V). Like the α-halo ester (V) the benzyl α-halo ester (XXVII) is reacted with a diamine to produce a piperazinone. The only difference is that both nitrogen atoms of the diamine (XXVIII) must be unsubstituted whereas with the α-halo ester (V) one of the diamine (VI) nitrogen atoms could be substituted ($R_{12}$). The benzyl piperazinone (XXIX) produced is then reacted with the amino blocking group, W', to produce the protected benzyl piperazinone (XXX). The protected benzyl piperazinone (XXX) is then reacted with an α-halo ester to obtain the protected benzyl piperazinone ester (XXXI). The alcohol portion of the ester (XXXI) is then replaced with the desired group Q. Q is hydroxyl, alkoxy where the alkyl group is 1 thru 3 carbon atoms, amino,

cycloalkyl substituted alkyl amino where the cycloalkyl substituted alkyl portion is 4 thru 7 carbon atoms, where $R_{13a}$ is a hydrogen atom or alkyl of 1 thru 4 carbon atoms and where $R_{13b}$ is alkyl of 1 thru 4 carbon atoms. It is preferred that Q is amino. The protecting group, W', is then removed to give the compound (XXXIII), which is then reacted with the protected tripeptide (XI) followed by removal of the protecting group to give the benzyl polypeptide piperazinone (XXXIV).

The benzyl group taken together with the carbon atom to which it is attached in the piperazinone ring as well as each of the adjacent groups (carbonyl and α-nitrogen) constitute phenylalanine. Therefore, the benzyl polypeptide piperazinone (XXXIV) contains phenylalanine in the piperazinone ring system.

When $R_4$ is iso-butyl and Q is hydroxyl the non-tripeptide group attached to the piperazinone is leucine. When $R_4$ is $CH_3$—S—$CH_2CH_2$— the group is methionine. It is preferred that $R_4$ is iso-butyl or $CH_3$—S—$CH_2CH_2$—. When Q is amino (preferred) the group is the amide of the coresponding amino acid. Hence, when $R_1$ is a hydrogen atom, $R_2$ is a methyl group, $R_4$ is iso-butyl and Q is amino the benzyl polypeptide piperazinone (XXXIV) can be represented as the amide of Tyr—D-ala—gly—L-phe cyclized as a piperazinone —leu When $R_1$, $R_2$ and Q are as above but $R_4$ is $CH_3$—S—$CH_2CH_2$— the benzyl polypeptide piperazinone (XXXIV) can be represented as the amide of Tyr—D-ala—gly—L-phe cyclized as a piperazinone —met When $R_1$, $R_4$ and Q are as in the above 2 cases but $R_2$ is a hydrogen atom the benzyl polypeptide piperazinone (XXXIV) can be represented as the amide of Tyr—gly—gly—L-phe cyclized as a piperazinone —leu and Tyr—gly—gly—L-phe cyclized as a piperazinone —met Therefore, the benzyl polypeptide piperazinones (XXXIV) have the first 3 amino acids in a chain, the fourth (phenylalanine) cyclized into a piperazinone ring and the fifth on the opposite side of the piperazinone ring from the tripeptide.

Chart E discloses a process to produce dehydrophenylalanine polypeptide piperazinones (XXXIX). The azlactone starting material (XXXV) is known. The azlactone is reacted with the appropriate piperazinone (VII) under reflux to give the protected dehydrophenylalanine piperazinone (XXXVI) which is transformed by previously described reactions (1) removal of protecting group, W, (2) addition of protected dipeptide (XXXVIII) and (3) removal of the protecting group to give the desired dehydrophenylalanyl polypeptide piperazinone (XXXIX).

CHART E
Preparation of Dehydrophenylalanyl Piperazinones

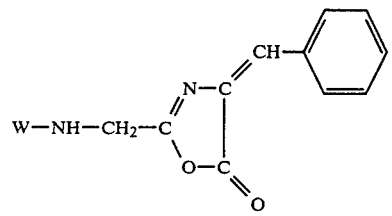
(XXXV)

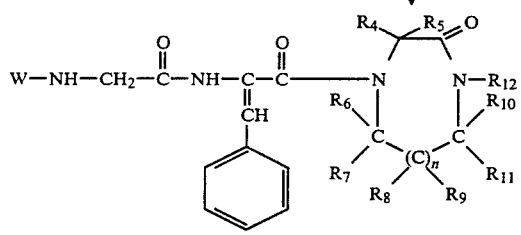
(XXXVI)

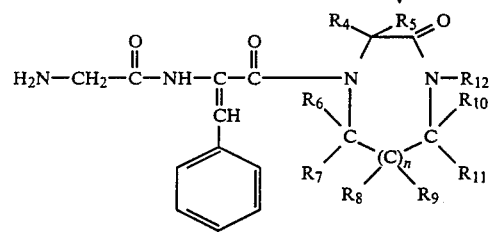
(XXXVII)

(1) protected dipeptide (XXXVIII)
(2) remove protecting group

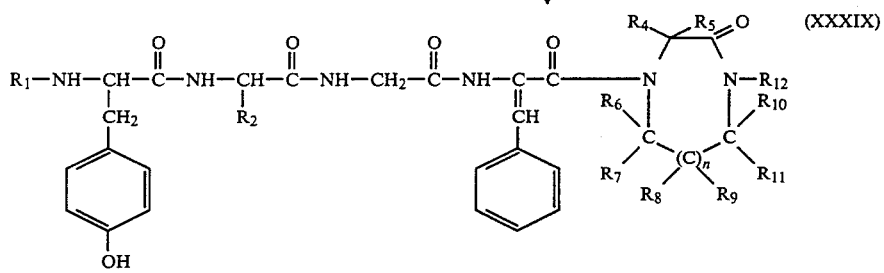
(XXXIX)

Charts F1 and F2 disclose a process to produce polypeptide piperazines (XLV). Piperazine refers to the compounds of formula (XLV) where n is 0, when n is 1 the compounds of formula (XLV) are actually hexahydro-1,4-diazepines, however for simplicity both series of compounds (n is 0 and 1) will be referred to as "piperazines". The 4-benzyl piperazinone (XL) is reduced with lithium aluminum hydride or similar reducing agent in the usual manner for reduction of an amide carbonyl group to give the piperazine (XLI) which then is protected (XLII) followed by removal of the benzyl group to give the protected piperazine (XLIII). The protected piperazine (XLIII) is reacted in the same way as the piperazinone (VII) to add first L-phenylalanine and then with the protected tripeptide (XI) followed by removal of the protecting group to produce the polypeptide piperazine (XLV).

CHART F1
Preparation of Piperazine Compounds

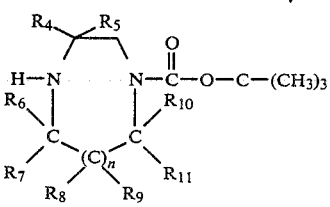
(XL)

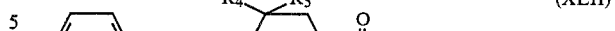
-continued
CHART F1
Preparation of Piperazine Compounds (XLII)

Chart F2
(XLII)

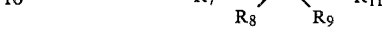

(XLIII)

(XLIV)

(1) Protected tripeptide
(2) Remove protecting group (XI)

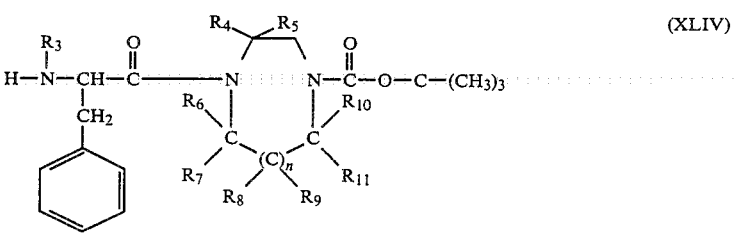
(XLV)

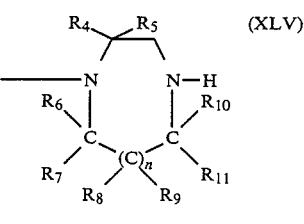

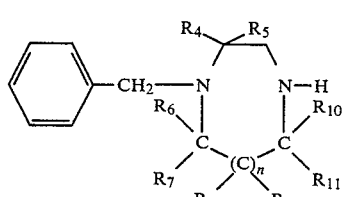
(XLI)

The starting materials (I, XIII, XVIII, VIIB, XXIV, XXXV and XL) are either known to those skilled in the art or can be readily prepared by methods well known to those skilled in the art from known compounds.

Most of the intermediates and the biologically active products (XII, XXXIV, XXXIX and XLV) are amines and therefore can exist in their free base form or as a salt. The pharmaceutically useful piperazinones (XII, XXXIV and XXXIX) and piperazines (XLV) are useful both as the free base and as a pharmaceutically acceptable salt. Since the amine intermediates are useful as intermediates and not as pharmaceuticals they are useful even in a salt form which may not be pharmaceutically acceptable and therefore the salt forms of the intermediate amines do not have to be limited to pharmaceutically acceptable salts.

The biologically active polypeptide piperazinones (XII, XXXIV and XXXIX) and polypeptide piperazines (XLV) are useful as analgesics and as psychotherapeutic agents. As analgesics they are useful in treating severe pain. As psychotherapeutic agents they are useful in treating anxiety, depression and psychosis.

The polypeptides (XII, XXXIV, XXXIX and XLV) are administered to a useful warm blooded animal, including man, parenterally. Since these agents are given parenterally the concentration of the active ingredient must be adjusted such that a single injection or IV feed will deliver the desired therapeutic amount as is well known to those skilled in the art.

When given as a single injection, the injection should deliver about 0.1 to about 10 mg./kg. When administered as an IV, the concentration and flow rate should be adjusted to deliver to the patient about 0.025 to about 2.5 mg./kg./hr.

The exact dose to be administered depends on the particular chemical agent (XII, XXXIV, XXXIX or XLV), the particular condition to be treated, the severity of the condition, the weight, age and condition of the patient, whether or not the patient is receiving any other drugs, etc. as is well known to those skilled in the art.

The definitions and explanations below are for the terms as used throughout the entire patent application including both the specification and claims.

All temperatures are in degrees Centigrade.
TLC refers to thin-layer chromatography.
THF refers to tetrahydrofuran.
DMF refers to dimethylformamide.
SSB refers to an isomeric mixture of hexanes.
p-TSA refers to p-toluenesulfonic acid.
Saline refers to an aqueous saturated sodium chloride solution.

Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.

When solvent pairs are used, the ratio of solvents used are volume/volume (v/v).

A is a chlorine or bromine atom.
R is a primary or secondary alkyl group of 1 thru 6 carbon atoms, cyclohexyl or phenyl.
$R_1$ is a hydrogen atom, methyl group or L-arginyl

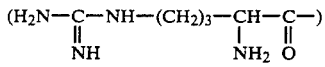

$R_2$ is a hydrogen atom, alkyl of 1 thru 3 carbon atoms, hydroxyalkyl where the alkyl portion is 1 thru 3 carbon atoms or $R_{2a}$—S—$R_{2b}$— with the proviso that when $R_2$ is not a hydrogen atom the carbon atom to which $R_2$ is attached is of the D configuration.
$R_{2a}$ is alkyl of 1 thru 3 carbon atoms.
$R_{2b}$ is alkyl of 1 thru 3 carbon atoms.
$R_3$ is a hydrogen atom or methyl group.
$R_4$ is a hydrogen atom, alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms.
$R_{4a}$ is alkyl of 1 thru 3 carbon atoms.
$R_{4b}$ is alkyl of 1 thru 3 carbon atoms.
$R_4'$ is alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms.
$R_5$, $R_6$, $R_7$, $R_8$, $R_9$, $R_{10}$, $R_{11}$, $R_{12}$ are when present independently a hydrogen atom, alkyl of 1 thru 4 carbon atoms, cycloalkyl of 3 thru 5 carbon atoms, cycloalkyl substituted alkyl of 4 thru 7 carbon atoms total with the proviso that the total number of carbon atoms in all these groups together when present is 0 thru 10.
$R_5'$ is alkyl of 1 thru 4 carbon atoms, cycloalkyl of 3 thru 5 carbon atoms, cycloalkyl substituted alkyl of 4 thru 7 carbon atoms total with the proviso that the total number of carbon atoms of $R_5'$ and $R_6$-$R_{12}$ together when present is 1 thru 10.
$R_{13a}$ is a hydrogen atom or alkyl of 1 thru 4 carbon atom.
$R_{13b}$ is alkyl of 1 thru 4 carbon atoms.
Q is hydroxyl, alkoxy where the alkyl group is 1 thru 3 carbon atoms, amino,

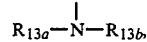

cycloalkyl substituted alkylamino where the cycloalkyl substituted alkyl portion is 4 thru 7 carbon atoms.

X is a chlorine or bromine atom.
W is an amino blocking group selected from the group consisting of benzyloxycarbonyl or t-butoxycarbonyl.
W' is W or benzyl.
n is 0 or 1.
Piperazinone refers to compounds of the formula (VII, IX, X, XII–XXIII, XXIX–XXXIV, XXXVI, XXXVII, XXXIX–XL) whether n is 0 or 1. It is realized that when n is 1 the compounds are hexahydro-2H-1,4-diazepin-2-ones.

Piperazine refers to compounds of the formula (XLI–XLV) whether n is 0 or 1. It is realized that when n is 1 the compounds are hexahydro-1,4-diazepines.

The chemical formulas of compounds of the present invention do not as drawn specify any particular stereochemical designation or identify any particular isomer, but are meant to and do include both isomers of the piperazinone or piperazine ring system ($R_4 \neq R_5$).

When the term alkyl of __ thru __ carbon atoms is used it is meant to and does include isomers thereof when such exist.

The compounds of the present invention (intermediates and biologically active products) can be isolated in either the free base or salt form as a solvate. Therefore, whenever a formula of a compound or its name is used in both the specification and claims it is meant to and does include solvates. The solvates are useful in the same manner as the non-solvated compounds.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

4-Methylpentanoic acid (III)

A mixture of potassium cyanide (100 g.) in water (100 ml.) is added to a stirred mixture of isoamyl bromide (I, 170 g.) in alcohol (400 ml.). The reaction mixture is refluxed for two days and then cooled and diluted with water (600 ml.). The mixture is extracted with ether (3×250 ml.). The combined ether extract is washed with water (2×) and the ether is removed under reduced pressure. The crude isoamyl nitrile thus obtained is mixed with alcohol (300 ml.), water (30 ml.), and potassium hydroxide (100 g.). The resulting mixture is heated under reflux for 24 hours and cooled. The cooled mixture is diluted with water (300 ml.) and extracted twice with ether. The aqueous phase is acidified with concentrated hydrochloric acid and extracted twice with ether. The combined ether extract is washed with water and saline. The ether is removed under reduced pressure and the residual liquid distilled to give the title compound, b.p. 115°/30 mm.

EXAMPLE 2

2-Bromo-4-methylpentanoyl chloride (IV)

A mixture of 4-methylpentanoic acid (III, Example 1, 46.4 g.) and thionyl chloride (59.5 g.) is heated under reflux for two hours. The mixture is cooled, bromine (63.9 g.) is added and the reaction mixture refluxed for three hours. Distillation under reduced pressure gives the α-bromo acid halide, b.p. 100°/30 mm.

EXAMPLE 3

Methyl-2-bromo-4-methylpentanoate (V)

2-Bromo-4-methylpentanoyl chloride (IV, Example 2) is added dropwise to methyl alcohol (200 ml.) at 0°. After two hours the methanol is removed under reduce pressure and the residual oil is partitioned between chloroform and water. The chloroform is separated from the water and removed under reduced pressure to give a residual oil which is distilled under reduced pressure to give the title compound, b.p. 78°–90°/30 mm.

EXAMPLE 4

3-(2-Methylpropyl)piperazinone (VII)

A mixture of methyl 2-bromo-4-methylpentanoate (V, Example 3, 14.6 g.) and ethylenediamine (VI, 12.5 g.) in ethanol (250 ml.) is stirred at 20°–25° for 20 hours. The ethanol is removed under reduced pressure and the residual oil is partitioned between chloroform and aqueous sodium bicarbonate. The chloroform layer is separated and the chloroform is removed under reduced pressure to give an oil which is refluxed in DMF (20 ml.) for one hour. After removal of the DMF the residue is column chromatographed on silica gel eluting with chloroform-methanol (99/5). Appropriate fractions are pooled and concentrated to give a residue which is dissolved in ethyl acetate (150 ml.) and decolorized with charcoal. Crystallization from ethyl acetate-SSB gives an oily solid which upon crystallization from ethyl acetate-SSB gives the title compound, m.p. 75°–77°.

EXAMPLE 5

Hexahydro-3-(2-methylpropyl)-2H-1,4-diazepin-2-one (VII)

Following the general procedure of Example 4, and making non-critical variations, but substituting 1,3-diaminopropane (VI) for ethylenediamine (VI) there is obtained hexahydro-3-(2-methylpropyl)-2H-1,4-diazepir-2-one, m.p. 112°–113°.

EXAMPLE 6

6,6-Dimethyl-3-(2-methylpropyl)piperazinone (VII)

Following the general procedure of Example 4 and making non-critical variations, but substituting 1,2-diamino-2-methylpropane (VI) for ethylenediamine (VI) there is obtained 6,6-dimethyl-3-(2-methylpropyl)-piperazinone, m.p. 140°–144°.

EXAMPLE 7

5,5-Dimethylpiperazinone and 6,6-dimethylpiperazinone (VII)

Following the general procedure of Example 4 and making non-critical variations, but substituting ethyl chloroacetate (VI) for methyl 2-bromo-4-methylpentanoate (V) and 1,2-diamino-2-methylpropane (VI) for ethylenediamine (VII) there are obtained 5,5-dimethylpiperazinone and 6,6-dimethylpiperazinone.

EXAMPLE 8

4[(S)-2-Amino-1-oxo-3-phenylpropyl)-3-[(S)-2-methylpropyl]piperazinone and 4[(S)-2-amino-1-oxo-3-phenylpropyl)-3[(R)-2-methylpropyl]piperazinone (X)

Dicyclohexylcarbodiimide (10.8 g.) is added to a stirred mixture of benzyloxycarbonyl L-phenylalanine (15. g.) in THF (250 ml.). After 5 minutes, 3-(2-methylpropyl)piperazinone (VII, Example 4, 8.2 g.) is added. After 2 hours, the solution is filtered to remove dicyclohexylurea. Chromatography on silica gel using chloroform as the eluant gives the protected product as an oil. This is dissolved in methanol (200 ml.), palladium/charcoal (10%, 5.0 g.) is added, and the solution is hydrogenated (50 lb. initial hydrogen pressure) for 30 minutes. The mixture is filtered, the catalyst is washed with methanol, and the methanol is removed under reduced pressure. The residual oil was applied to a silica gel column which is eluted with methanolic-ammonia chloroform (5/95) to give 4-[(S)-2-amino-1-oxo-3-phenylpropyl]-3-[(S)-2-methylpropyl]piperazinone which is recrystallized from ethyl acetate-SSB to give the title compound, m.p. 137°–139°; $[\alpha]_D^{25} + 147°$ (CH$_3$OH, C=1). Structure confirmed by x-ray diffraction.

The column was further eluted with methanolic ammonia-chloroform (10/90) and (20/80) to give 4-[(S)-2-amino-1-oxo-3-phenylpropyl]-3-[(R)-2-methylpropyl]-piperazinone which is recrystallized from ethyl acetate to give the title compound, m.p. 147°–149°; $[\alpha]_D^{25} - 15°$ (CH$_3$OH, C=1).

EXAMPLE 9

4-[(S)-2-amino-1-oxo-3-phenylpropyl]-3-[(S)-2-methyl-propyl]piperazinone and
4[(S)-2-amino-1-oxo-3-phenylpropyl]-3-[(R)-2-methyl-propyl]piperazinone (X)

Dicyclohexylurea (2.06 g., 0.01 mole) is added to a stirred solution of t-butoxycarbonyl-L-phenylalanine (VIII, 2.65 g., 0.01 mole) in THF (25 ml.) at 0°. A solution of 3-(2-methylpropyl)piperazinone (VII, Example 4, 1.56 g., 0.01 mole) in THF (20 ml.) is added and the mixture is stirred for 4 hours, filtered to remove dicyclohexylurea and the filtrate concentrated to give an oil, which is dissolved in chloroform and column chromatographed on silica gel to remove dicyclohexylurea. The appropriate fractions are pooled and concentrated. The purified material is dissolved in trifluoroacetic acid (20 ml.). After 1 hour the bulk of the trifluoroacetic acid was removed under reduced pressure and the residue is partitioned between chloroform and sodium hydroxide (1N) solution. The chloroform is washed with water and removed under reduced pressure. Chromatography of the concentrate on silica gel gives 4-[(S)-2-amino-1-oxo-3-phenylpropyl]-3-[(S)-2-methylpropyl]piperazinone, m.p. 137°–139° and 4-[(S)-2-amino-1-oxo-3-phenylpropyl]-3-[(R)-2-methyl-propyl]piperazinone, m.p. 147°–149°.

EXAMPLE 10

4-[(S)-2-amino-1-oxo-3-phenylpropyl]piperazinone (X)

Following the general procedure of Example 9, and making non-critical variations, but substituting piperazinone (VII, prepared as described by S. R. Aspinal, J. Am. Chem. Soc., 62, 1202 (1940) for 3-(2-methylpropyl)piperazinone (VII) there is obtained 4-[(S)-2-amino-1-oxo-3-phenylpropyl]piperazinone, m.p. 78°–80°.

EXAMPLE 11

4-[(S)-2-amino-1-oxo-3-phenylpropyl]-3-[(S)-methyl]-piperazinone and
4-[(S)-2-amino-1-oxo-3-phenylpropyl]-3-[(R)-methyl]-piperazinone (X)

Following the general procedure of Example 9, and making non-critical varations, but substituting 3-methylpiperazinone (VII, prepared as described by S. Kawahara and H. Kawakami, Yagugaku Zasshi, 82, 909 (1962) for 3-(2-methylpropyl)piperazinone (VII) there is obtained 4-[(S)-2-amino-1-oxo-3-phenylpropyl]-3-[(S)-methyl]piperazinone hemihydrate, m.p. 115°–130° and 4-[(S)-2-amino-1-oxo-3-phenylpropyl]-3-[(R)-methyl]piperazinone hemihydrate, m.p. 101°–103°.

EXAMPLE 12

4-[(S)-2-amino-1-oxo-3-phenylpropyl]-1-methyl-3-[(S)-2-methylpropyl]piperazinone and
4-[(S)-2-amino-1-oxo-3-phenylpropyl]-1-methyl-3-[(R)-2-methylpropyl]piperazinone (X)

Following the general procedure of Example 9 and making non-critical variations, but substituting 1-methyl-3-(2-methylpropyl)piperazinone (VII) for 3-(2-methylpropylpiperazinone there is obtained 4-[(S)-2-amino-1-oxo-3-phenylpropyl]-1-methyl-3-[(S)-2-methylpropyl]piperazinone (X) m.p. 105°–107° and 4-[(S)-2-amino-1-oxo-3-phenylpropyl]-1-methyl-3-[(R)-2-methylpropyl]piperazinone, m.p. 131°–133°.

EXAMPLE 13

Hexahydro
4-[(S)-2-amino-1-oxo-3-phenylpropyl]-3-[(S)-2-methyl-propyl]-2H-1,4-diazepin-2-one and
hexahydro-4-[(S)-2-amino-1-oxo-3-phenylpropyl]-3-[(R)-2-methylpropyl]-2H-1,4-diazepin-2-one (X)

Following the general procedure of Example 9 and making non-critical variations, but substituting hexahydro-3-(2-methylpropyl)-2H-1,4-diazepin-2-one (VII) for 3-(2-methylpropyl)piperazinone (VII) there is obtained hexahydro-4-[(S)-2-amino-1-oxo-3-phenylpropyl]-3-[(S)-2 methylpropyl]-2H-1,4-diazepin-2-one, m.p. 116°–119° and hexahydro-4-[(S)-2-amino-1-oxo-3-phenylpropyl]-3-[(R)-2-methylpropyl]-2H-1,4-diazepin-2-one hemihydrate, m.p. 84°–87°.

EXAMPLE 14

4-[(S)-2-amino-1-oxo-3-phenylpropyl)-6,6-dimethyl-3-[(S)-2-methylpropyl]piperazinone and
4-[(S)-2-amino-1-oxo-3-phenylpropyl)-6,6-dimethyl-3-[(R)-2-methylpropyl]piperazinone (X)

Following the general procedure of Example 9 and making non-critical variations, but substituting 6,6-dimethyl-3-(2-methylpropyl)piperazinone (VII) for 3-(2-methylpropyl)piperazinone (VII) there is obtained 4-[(S)-2-amino-1-oxo-3-phenylpropyl)-6,6-dimethyl-3-[(S)-2-methylpropyl]piperazinone monohydrate, m.p. 80°–85° and 4-[(S)-2-amino-1-oxo-3-phenylpropyl)-6,6-dimethyl-3-[(R)-2-methylpropyl]piperazinone, m.p. 134°–136°.

EXAMPLE 15

4-[(S)-2-methylamino-1-oxo-3-phenylpropyl]-3-[(S)-2-methylpropyl]piperazinone and
4-[(S)-2-methylamino-1-oxo-3-phenylpropyl]-3-[(R)-2-methylpropyl]piperazinone (X)

Following the general procedure of Example 9 and making non-critical variations, but substituting t-butoxycarbonyl-N-methyl-L-phenylalanine (VIII) for t-butoxycarbonyl-L-phenylalanine (VIII) there is obtained 4-[(S)-2-methylamino-1-oxo-3-phenylpropyl]-3-[(S)-2-methylpropyl]-piperazinone, m.p. 158°–159° and 4-[(S)-2-methylamino-1-oxo-3phenylpropyl]-3-[(R)-2-methylpropyl]piperazinone, m.p. 134°–136°.

EXAMPLE 16

4-[(S)-2-amino-1-oxo-3-phenylpropyl]-3-[(S)-2-(methylthio)ethyl]piperazinone and
4-[(S)-2-amino-1-oxo-3-phenylpropyl]-3-[(R)-2-(methylthio)ethyl]piperazinone (X)

Following the general procedure of Example 9 and making non-critical variations, but substituting 3-[2-(methylthio)ethyl]piperazinone for 3-[2-methylpropyl]-piperazinone there is obtained 4-[(S)-2-amino-1-oxo-3-phenylpropyl]-3-[(S)-2-(methylthio)ethyl]piperazinone and 4-[(S)-2-amino-1-oxo-3-phenylpropyl]-3-[(R)-2-(methylthio)ethyl]piperazinone.

EXAMPLE 17

4-[(S)-2-amino-1-oxo-3-phenylpropyl]-6,6-dimethyl-piperazinone (X)

Following the general procedure of Example 9 and making non-critical variations, but substituting 6,6-dimethylpiperazinone (VII) for 3-(2-methylpropyl)- piperazinone (VII) there is obtained 4-[(S)-2-amino-1-oxo-3-phenylpropyl]-6,6-dimethylpiperazinone.

EXAMPLE 18 t-Butoxycarbonyl-O-(2,6-dichlorobenzyl)-L-tyrosyl-D-alanylglycine (XI)

Step 1—D-Alanylglycine methyl ester, hydrochloride

Dicyclohexylcarbodiimide (15.9 g.) is added to a mixture of t-butoxycarbonyl D-alanine (13.2 g.), glycine methyl ester hydrochloride (10.6 g.) and triethylamine (10.7 ml.) in DMF (300 ml.), chilled to 0° on an ice-water bath and stirred via magnetic stirrer. After four hours the mixture is allowed to warm to 20°–25° overnight.

Acetone is added and the dicyclohexylurea is removed by filtration. The filtrate was concentrated on a rotary evaporator to an oil. A solution of the residue in ethyl acetate (300 ml.) is washed with two volumes (500 ml. each) of 1N hydrochloric acid, three volumes (400 ml. each) of 10% sodium carbonate, and deionized water (100 ml.). Each aqueous solution was back-washed with two volumes (300 ml. each) of ethyl acetate. The ethyl acetate solutions are combined and concentrated on a rotary evaporator to give t-butoxycarbonyl D-alanylglycine methyl ester as an oil.

The oil is added to a saturated methanolic hydrogen chloride solution (400 ml.) and the solution is allowed to stand until the starting material is no longer detectable by TLC. The solution was concentrated on a rotary evaporator to an oil, which was triturated with ether (400 ml.) to give D-alanylglycine methyl ester hydrochloride.

Step 2—t-Butoxycarbonyl-O-(2,6-dichlorobenzyl)-tyrosyl-D-alanylglycine methyl ester Dicyclohexylcarbodiimide (16.5 g.) is added to a mixture of t-butoxycarbonyl-O-(2,6-dichlorobenzyl)-tyrosine (35.2 g.), D-alanylglycine methyl ester hydrochloride (Step 1, 15.6 g.), 1-hydroxybenzotrazole monohydrate (12.2 g.) and triethylamine in DMF (300 ml.) chilled to 0° on an ice-water bath and stirred with a magnetic stirrer. After four hours the mixture is allowed to warm to 20°–25° overnight.

Acetone (300 ml.) is added and the precipitate of dicyclohexylurea is removed by filtration. The filtrate is concentrated on a rotary evaporator to an oil. A solution of the residue in ethyl acetate (800 ml.) is washed with 1N hydrochloric acid (1.5 l.), two volumes (1.5 l. each) of 10% sodium carbonate, and deionized water (500 ml.). Chloroform is added during the water wash to prevent product from oiling out. Each aqueous solution is back-washed with two volumes (1 l. each) of chloroform. The organic solutions are combined and concentrated on a rotary evaporator to a crystalline solid. The solid is triturated with ethyl ether (1 liter), filtered and dried to give t-butoxycarbonyl-O-(2,6-dichlorobenzyl)tyrosyl-D-alanylglycine methyl ester.

Step 3—t-Butoxycarbonyl-O-(2,6-dichlorobenzyl)-L-tyrosyl-D-alanylglycine (XI)

Aqueous 1N sodium hydroxide (12 ml.) is added to a suspension of t-butoxycarbonyl-O-(2,6-dichlorobenzyl)-L-tyrosyl-D-alanylglycine methyl ester (Step 2, 4.7 g.) in acetone (25 ml.) stirred with a magnetic stirrer. After 4½ hours the solution is acidified to pH 2 with 4N hydrochloric acid. After an hour a white precipitate is removed by filtration and dried under vacuum to give t-butoxycarbonyl-O-(2,6-dichlorobenzyl)-L-tyrosyl-D-alanylglycine.

EXAMPLE 19

3-[(R)-2-methylpropyl]-4-(L-tyrosyl-D-alanylglycyl-L-phenylalanyl)piperazinone (XII)

Dicyclohexylcarbodiimide (309 mg.) is added at 0° to a stirred solution of t-butoxycarbonyl-O-(2,6-dichlorobenzyl)-L-tyrosyl-D-alanylglycine (XI, Example 18, 614 mg.), 4-[(S)-2-amino-1-oxo-3-phenylpropyl]-3-[(R)-2-methylpropyl]piperazinone (X, Example 8, 455 mg.) and 1-hydroxybenzotrazole monohydrate (230 mg.) in DMF (10 ml.). The mixture is allowed to warm to 20°–25° overnight. Acetone (20 ml.) is added and dicyclohexylurea is removed by filtration. The filtrate is concentrated on a rotary evaporator. The residue is triturated with ethyl acetate (25 ml.) and additional dicyclohexylurea is removed by filtration. The filtrate is washed with 1N hydrochloric acid (75 ml.), two volumes (75 ml. each) of 10% sodium carbonate, and deionized water (30 ml.). The ethyl acetate layers are combined and concentrated on a rotary evaporator to an oil which solidified under vacuum to give 4-t-butoxycarbonyl-O-(2,6-dichlorobenzyl)-L-tyrosyl-D-alanylglycyl-L-phenylalanyl-3-[(R)-2-methylpropyl]-piperazinone as a powder.

The powder (0.5 g.) is dissolved in anisole (4 ml.) and anhydrous hydrogen fluoride (4 ml.) is added to the cooled solution. The mixture is allowed to stir at 0° in an ice-water bath for one hour. Hydrogen fluoride is distilled off under vacuum. The residue is dissolved in glacial acetic acid (30 ml.) and water (5 ml.). Diethyl ether (30 ml.) and water (30 ml.) are added and the mixture vigorously shaken. The aqueous layer is removed and washed with ethyl ether (30 ml.). Both ether layers are back-washed with 1N acetic acid (30 ml.). The acetic acid solutions were combined and lyophilized to a white powder.

A column of Sephadex G-10 (60 g.) is equilibrated in the lower phase of a mixture of butanol, acetic acid and water (4:1:5). Excess lower phase is displaced by elution with the upper phase of the 4:1:5 mixture. The crude peptide is applied to the column in a minimum volume of upper phase 4:1:5 solution, and eluted with upper phase, collecting 5 ml. fractions. TLC analysis shows the major band eluted in fractions 13–17. These fractions are combined, concentrated on a rotary evaporator, and lyophilized from aqueous acetic acid to give the title compound as a mixture of the acetate and fluoride salts.

EXAMPLE 20

3[(S)-2-methylpropyl]-4-(L-tyrosyl-D-alanylglycyl-L-phenylalanyl)piperazinone (XII)

Following the general procedure of Example 19 and making non-critical variations, but substituting 4-[(S)-2-amino-1-oxo-3-phenylpropyl]-3-[(S)-2-methylpropyl]-piperazinone (X, Example 8) for 4-[(S)-2-amino-1-oxo-3-phenylpropyl]-3-[(R)-2-methylpropyl]piperazinone (X) there is obtained 3-[(S)-2-methylpropyl]-4-(L-tyrosyl-D-alanylglycyl-L-phenylalanyl)piperazinone as a mixture of the acetate and fluoride salt.

EXAMPLE 21

4-(L-tyrosyl-D-alanylglycyl-L-phenylalanyl)piperazinone (XII)

Following the general procedure of Example 19 and making non-critical variations, but substituting 4-[(S)-2-amino-1-oxo-3-phenylpropyl]piperazinone (X, Example 10) for 4-[(S)-2-amino-1-oxo-3-phenylpropyl]-3-[(R)-2-methylpropyl]piperazinone there is obtained 4-(L-tyrosyl-D-alanylglycyl-L-phenylalanyl)piperazinone as a mixture of the acetate and fluoride salts.

EXAMPLE 22

3-[(S)-Methyl]-4-(L-tyrosyl-D-alanylglycyl-L-phenylalanyl)piperazinone (XII)

Following the general procedure of Example 19 and making mon-critical variations, but substituting 4-[(S)-2-amino-1-oxo-3-phenylpropyl]-3-[(S)-methyl]piperazinone (X, Example 11) for 4-[(S)-2-amino-1-oxo-3-phenylpropyl]-3-[(R)-2-methylpropyl]piperazinone (X) there is obtained 3-[(S)-methyl]-4-(L-tyrosyl-D-alanylglycyl-L-phenylalanyl)piperazinone as a mixture of the fluoride and acetate salts.

EXAMPLE 23

3-[(R)-Methyl]-4-(L-tyrosyl-D-alanylglycyl-L-phenylalanyl)piperazinone (XII)

Following the general procedure of Example 19 and making non-critical variations, but substituting 4-[(S)-2-amino-1-oxo-3-phenylpropyl]-3-[(R)-methyl]piperazinone (X, Example 11) for 4-[(S)-2-amino-1-oxo-3-phenylpropyl]-3-[(R)-2-methylpropyl]piperazinone (X) there is obtained 3-[(R)-methyl]-4-(L-tyrosyl-D-alanylglycyl-L-phenylanalyl)piperazinone as a mixture of the acetate and fluoride salts.

EXAMPLE 24

1-Methyl-3-[(S)-2-methylpropyl]-4-(L-tyrosyl-D-alanylglycyl-L-phenylalanyl)piperazinone (XII)

Following the general procedure of Example 19 and making non-critical variations, but substituting 4-[(S)-2-amino-1-oxo-3-phenylpropyl]-1-methyl-3-[(S)-2-methylpropyl]piperazinone (X, Example 12) for 4-[(S)-2-amino-1-oxo-3-phenylpropyl]-3-[(R)-2-methylpropyl]piperazinone (X) there is obtained 1-methyl-3-[(S)-2-methylpropyl]-4-(L-tyrosyl-D-alanylglycyl-L-phenylalanyl)piperazinone as a mixture of the acetate and fluoride salts.

EXAMPLE 25

1-Methyl-3-[(R)-2-methylpropyl]-4-(L-tyrosyl-D-alanylglycyl-L-phenylalanyl)piperazinone (XII)

Following the general procedure of Example 19 and making non-critical variations, but substituting 4-[(S)-2-amino-1-oxo-3-phenylpropyl]-1-methyl-3-[(R)-2-methylpropyl]piperazinone (X, Example 12) for 4-[(S)2-amino-1-oxo-3-phenylpropyl]-3-[(R)-2-methylpropyl]-piperazinone (X) there is obtained 1-methyl-3-[(R)-2-methylpropyl]-4-(L-tyrosyl-D-alanylglycyl-L-phenylalanyl)piperazinone as a mixture of the acetate and fluoride salts.

EXAMPLE 26

Hexahydro-3-[(S)-2-methylpropyl]-4-(L-tyrosyl-D-alanylglycyl-L-phenylalanyl)-2H-1,4-diazepin-2-one (XII)

Isobutyl chloroformate (137 mg., 0.001 mole) is added to a stirred solution of t-butoxycarbonyl-L-tyrosyl-D-alanylglycine (XI, 400 mg., 0.002 mole, prepared as described by Belgium Patent 850,941) and N-methyl morpholine (100 mg., 0.001 mole) in THF (20 ml.) at −10°. After 10 minutes a solution of hexahydro 4-[(S)-2-amino-1-oxo-3-phenylpropyl]-3-[(S)-2-methylpropyl]-2H-1,4-dizepine-2-one (X, Example 13, 350 mg., 0.0011 mole) in THF (5 ml.) is added and the reaction mixture is stirred at 20°-25° for 4 hours. The THF is removed under reduced pressure and the residual oil is partitioned between ethyl acetate and water. The ethyl acetate is washed with 0.1N hydrochloric acid (20 ml.), 1.0M sodium bicarbonate solution (10 ml.) and water (2×10 ml.). Evaporation of the chloroform gives an oil which is dissolved in chlorofrom and chromatographed on silica. Elution with methanol: chloroform (1:0) gives hexahydro-4-(t-butoxycarbonylamino-L-tryosyl-D-alanylglycyl-L-phenylalanyl)-3-[(S)-2-methylpropyl]-2H-1,4-diazepin-2-one.

The bulk of the product is dissolved in trifluoroacetic acid (5 ml.). After 45 minutes at 20°-25° the trifluoroacetic acid was removed under reduced pressure, the product is dissolved in water (200 ml.) and is extracted with ether (200 ml.). Lyophilization of the aqueous phase gives the title compound as the trifluoroacetate salt.

EXAMPLE 27

Hexahydro-3-[(R)-2-methylpropyl]-4-(L-tyrosyl-D-alanylglycyl-L-phenylalanyl)-2H-1,4-diazepin-2-one (XII)

Following the general procedure of Example 26 and making non-critical variations, but substituting hexahydro-4-[(S)-2-amino-1-oxo-3-phenylpropyl]-3-[(R)-2-methylpropyl]-2H-1,4-diazepin-2-one (X, Example 13) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 28

6,6-Dimethyl-3-[(S)-2-methylpropyl]-4-(L-tyrosyl-D-alanylglycyl-L-phenylalanyl)piperazinone (XII)

Following the general procedure of Example 26 and making non-critical variations, but substituting 4-[(S)-2-amino-1-oxo-3-phenylpropyl]-6,6-dimethyl-3-[(S)-2-methylpropyl]piperazinone (X, Example 14) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 29

6,6-Dimethyl-3-[(R)-2-methylpropyl]-4-(L-tyrosyl-D-alanylglycyl-L-phenylalanyl)piperazinone (XII)

Following the general procedure of Example 26 and making non-critical variations, but substituting 4-[(S)-2-amino-1-oxo-3-phenylpropyl]-6,6-dimethyl-3[(R)-2-methylpropyl]piperazinone (X, Example 14) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 30

3-[(S)-2-methylpropyl]-4-(L-tyrosyl-D-alanylglycyl-L-N-methylphenylalanyl)piperazinone Following the general procedure of Example 26 and making non-critical variations, but substituting 4-[(S)-2-methylamino-1-oxo-3-phenylpropyl]-3-[(S)-2-methylpropyl]piperazinone (X, Example 15) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 31

3-[(R)-2-methylpropyl]-4-(L-tyrosyl-D-alanylglycyl-L-N-methylphenylalanyl)piperazinone (XII)

Following the procedure of Example 26 and making noncritical variations, but substituting 4-[(S)-2-methylamino-1-oxo-3-phenylpropyl]-3-[(R)-2-methylpropyl]piperazinone (X, Example 15) for hexahydro-4-[(S)-2-amino-1-oxo-3-phenylpropyl]-3-(S)-2-methylpropyl]-2H-1,4-diazepin-2-one there is obtained the title compound as the trifluoroacetate salt.

EXAMPLE 32

3-[(S)-2-(methylthio)ethyl]-4-(L-tyrosyl-D-alanylglycyl-L-phenylalanyl)piperazinone (XII)

Following the general procedure of Example 26 and making non-critical variations, but substituting 4-[(S)-2-amino-1-oxo-3-phenylpropyl]-3-[(S)-2-(methylthio)ethyl]-piperazinone (X, Example 16) for hexahydro-4-[(S)-2-amino-1-oxo-3-phenylpropyl]-3-[(S)-2-methylpropyl]-2H-1,4-diazepin-2-one (X) ther is obtained the title compound as the trifluoroacetate salt.

EXAMPLE 33

3-[(R)-2-(methylthio)ethyl]-4-(L-tyrosyl-D-alanylglycyl-L-phenylalanyl)piperazinone (XII)

Following the general procedure of Example 26 and making non-critical variations, but substituting 4-[(S)-2-amino-1-oxo-3-phenylpropyl]-3-[(R)-2-(methylthio)ethyl]-piperazinone (X, Example 16) for hexahydro-3-[(S)-2-methylpropyl]-4-[(S)-2-amino-1-oxo-3-phenylpropyl]-2H-1,4-diazepin-2-one (X) there is obtained the title compound as the trifluoroacetate salt.

EXAMPLE 34

3-[(S)-2-(methylthio)ethyl]-4-(L-tyrosyl-D-alanylglycyl-L-N-methylphenylalanyl)piperazinone (XII)

Following the general procedure of Example 26 and making non-critical variations, but substituting 4-[(S)-2-methylamino-1-oxo-3-phenylpropyl]-3-[(S)-2-(methylthio)ethyl]piperazone (X, prepared by the process of Examples 15 and 82)for hexahydro-3-[(S)-2-methylpropyl]-4-[(S)-2-amino-1-oxo-3-phenylpropyl]-2H-1,4-diazepin-2-one (X) there is obtained the title compound as the trifluoroacetate salt.

EXAMPLE 35

3-[(R)-2-(methylthio)ethyl]-4-(L-tyrosyl-D-alanylglycyl-L-N-methylphenylalanyl)piperazinone (XII)

Following the general procedure of Example 26 and making non-critical variations, but substituting 4-[(S)-2-methylamino-1-oxo-3-phenylpropyl]-3-[(R)-2-methylthio)ethyl]piperazione (X, prepared by the process of Examples 15 and 82) for hexahydro-3-[(S)-2-methylpropyl-4-[(S)-2-amino-1-oxo-3-phenylpropyl]-2H-1,4-diazepin-2-one (X) there is obtained as the trifluoroacetate salt.

EXAMPLE 36

6,6-Dimethyl-4-(L-tyrosyl-D-alanylglycyl-L-phenylalanyl)piperazinone (XII)

Following the general procedure of Example 26 and making non-critical variations, but substituting 4-[(S)-2-amino-1-oxo-3-phenylpropyl]-6,6-dimethylpiperazinone (X, prepared by the process of Examples 10 and 14) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 37

5,5-Dimethyl-3-(2-methylpropyl)-4-(L-tyrosyl-D-alanylglycylphenylalanyl)piperazinone (XII)

Following the general procedure of Example 26 and making non-critical variations, but substituting 4-(2-amino-1-oxo-3-phenylpropyl-5,5-dimethyl-3-(2-methylpropyl)piperazinone (X, prepared by the process of Example 84) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 38

5,5-Dimethyl-4-(L-tyrosyl-D-alanylglycyl-phenylalanyl)piperazinone (XII)

Following the general procedure of Example 26 and making non-critical variations, but substituting 4-(2-amino-1-oxo-3-phenylpropyl)-5,5-dimethylpiperazinone (X, prepared by the process of Example 85) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 39

1,4-Bis(phenylmethyl)piperazinone, hydrochloride (XIII)

A mixture of N,N'-dibenzylethylenediamine (24.0 g., 0.1 mole), ethyl chloroacetate (V, 24.51 g., 0.2 mole), anhydrous sodium carbonate (10 g., 0.094 mole) in ethanol (250 ml.) is heated under reflux for 20 hours. The ethanol is removed under reduced pressure and the residue is partitioned between chloroform and water. Evaporation of the chloroform gives an oil which is dissolved in isopropanol (200 ml.) and acidified with ethereal hydrogen chloride. The precipitate of 1,4-bis(-phenylmethyl)piperazinone hydrochloride is filtered off and recrystallized from isopropanol, m.p. 209°–212°.

EXAMPLE 40

1-(Phenylmethyl)piperazinone hydrochloride (XIV)

A mixture of 1,4-bis(phenylmethyl)piperazinone hydrochloride (XIII, Example 39, 15.0 g.) and 10% palladium charcoal (5.0 g.) in ethanol (200 ml.) is hydrogenated (50 lb. initial hydrogen pressure) until uptake of hydrogen ceased. The solution is filtered, the ethanol is removed under reduced pressure and the residual solid is recrystallized from methanol-isopropanol to give the title compound, m.p. 160°–161°.

EXAMPLE 41

4-(t-Butoxycarbonyl)-1-(phenylmethyl)piperazinone (XV)

A mixture of 1-(phenylmethyl)piperazinone (XIV, Example 40, 19.0 g., 0.1 mole) and 2-(t-butoxycarbonyloxyimino)-2-phenylacetamide (30.0 g., 0.12 mole) in benzene (200 ml.) is heated under reflux for 1 hour. The benzene is removed under reduced pressure, the residual oil is dissolved in ethyl acetate:SSB (1:1) and chromatographed on silica gel. The column is eluted with ethyl acetate, the appropriate fractions are pooled, concentrated and the product is crystallized from ethyl acetate:SSB (1:10) to give the title compound, m.p. 89°–90°.

EXAMPLE 42

4-t-butoxycarbonyl-3-[2-(methylthio)ethyl]-1-(phenylmethyl)piperazinone (XVI)

Following the general procedure of Example 47 and making non-critical variations, but substituting 4-t-butoxycarbonyl-1-(phenylmethyl)piperazinone (XV, Example 41) for 1-methyl-4-(phenylmethyl)piperazinone and 1-chloro-2-(methylthio)ethane [Chem. Ber., 84, 911 (1951)] for 1-bromo-2-methylpropane, there is obtained the title compound.

EXAMPLE 43

4-t-Butoxycarbonyl-3-[2-(methylthio)ethyl]-piperazinone (XVII)

Sodium metal (1.3 g., 0.057 mole) is added to a stirred solution of 4-t-butoxycarbonyl-3-[2-(methylthio)ethyl]-1-(phenylmethyl)-2-piperazinone (XVI, Example 42, 3.71 g., 0.01 mole) in diglyme (100 ml.) and ammonia (500 ml.) at −60°. The solution is allowed to reflux for 2 hours, the ammonia is allowed to evaporate and the diglyme is removed at 20°–25° under reduced pressure. The residue is partitioned between diethylether and water. Evaporation of the diethylether gives the title compound.

EXAMPLE 44

3-[2-(methylthio)ethyl]piperazinone (VIIA)

Trifluoroacetic acid (30 ml.) is added at 0° to a stirred solution of 4-t-butoxycarbonyl-3-[2-(methylthio)ethyl]-piperazinone (XVII, Example 43, 2.6 g., 0.0095 mole) in diethyl sulfide (20 ml.). After 1 hour the solvents are removed and the residual oil is partitioned between chloroform (300 ml.) and 5N sodium hydrochloride solution (10 ml.). The chloroform is washed with water (2×10 ml.) and the chloroform is removed under reduced pressure. The residual oil is chromatographed on silica gel eluted with methanol:chloroform (1:9), the appropriate fractions are pooled and concentrated to give a solid which upon recrystallization from ethyl acetate:SSB gives the title compound, m.p. 68°–70°.

EXAMPLE 45

4-(phenylmethyl)piperazinone

A solution of ethyl chloroacetate (204 g., 1.67 mole) in ethanol (500 ml.) is added to a stirred solution of ethylenediamine (600 g., 10 mole) in ethanol (3 l.) at 0°. After addition is complete the solution is allowed to warm to 20°–25°. After 5 hours a solution of sodium methoxide (90.0 g., 1.67 mole) in methanol (200 ml.) is added and the solution is stirred overnight, filtered to remove inorganic salts and evaporated to remove solvent and unreacted ethylenediamine. The residual oil (189 g.) is added to a mixture of benzyl chloride (241 g., 1.9 mole) anhydrous sodium carbonate (191 g., 2.28 mole) in ethanol (2.3 l.) and the solution is stirred under reflux for 3 hours. The ethanol is removed under reduced pressure and the residue is partitioned between chloroform and water. Evaporation of the chloroform gave a crystalline product which was recrystallized from ethyl acetate to give the title compound, m.p. 154°–156°.

EXAMPLE 46

1-Methyl-4-(phenylmethyl)piperazinone

Sodium hydride (50% in oil, 10.4 g., 0.22 mole) is added to a stirred solution of 4-(phenylmethyl)piperazinone (Example 45, 38.0 g., 0.20 mole) in THF (2.0 l.). After 1 hour methyl iodide (80.0 g., 0.75 mole) is added and the reaction solution is refluxed for 2.5 hours. The THF is removed under reduced pressure and the residual oil is partitioned between chloroform and water. Evaporation of the chloroform gives an oil which is chromatographed on silica gel to give the title compound, which is converted to the p-ISA salt, m.p. 138°–140°.

EXAMPLE 47

1-Methyl-3-(2-methylpropyl)-4-(phenylmethyl)-piperazinone

Butyl lithium (8.0 ml. of 1.6M in hexane, 0.012 mole) is added at −60° to a stirred solution of 1-methyl-4-(phenylmethyl)piperazinone (Example 46, 2.04 g., 0.010 mole), diisopropylamine (1.1 g., 0.011 mole) and hexamethylphosphorotriamide (2.0 ml.) in THF (25 ml.). The solution is allowed to warm to 20°–25°, 1-bromo-2-methylpropane (4.1 g., 0.030 mole) is added and the solution is refluxed for 3 hours. The THF is removed under reduced pressure and the residual oil is partitioned between chloroform and water. Evaporation of the chloroform gives an oil which is dissolved in ethyl acetate and chromatographed on silica gel. Elution of the column with ethyl acetate and pooling of the appropriate fractions gives the title compound.

EXAMPLE 48

1-Methyl-3-(2-methylpropyl)piperazinone

1-Methyl-3-(2-methylpropyl-4-(phenylmethyl)-piperazinone (Example 47, 2.1 g.) is dissolved in methanol (200 ml.), 10% palladium charcoal (1.0 g.) is added and the product is hydrogenated (50 lb. initial hydrogen pressure until the uptake of hydrogen ceased. The solution is filtered and the methanol is removed under reduced pressure to give the title compound as an oil.

EXAMPLE 49

3-Methyl-1,4-bis(phenylmethyl)piperazinone hydrochloride (XVIII)

Following the general procedure of Example 39 and making non-critical variations, but substituting ethyl-2-chloropropionate (V) for ethyl chloroacetate (V) there is obtained the title compound, m.p. 160°–162°.

EXAMPLE 50

3-(2-Methylpropyl)-1,4-bis(phenylmethyl)piperazinone (XVIII)

Following the general procedure of Example 47 and making non-critical variations, but substituting 1,4-bis(phenylmethyl)piperazinone (XIII, Example 39) for 1-methyl-4-(phenylmethyl)piperazinone there is obtained the title compound.

EXAMPLE 51

3-Methyl-3-(2-methylpropyl)-1,4-bis(phenylmethyl)-piperazinone (XXI)

Following the general procedure of Example 47 and making non-critical variations, but substituting 3-methyl-1,4-bis(phenylmethyl)piperazinone (XVIII, Example 49) for 1-methyl-4-(phenylmethyl)piperazinone there is obtained the title compound, m.p. 98°–101°.

EXAMPLE 52

3-Methyl-3-(2-methylpropyl)-4-(phenylmethyl)-piperazinone (XXII)

Following the general procedure of Example 43 and making non-critical variations, but substituting 3-methyl-3-(2-methylpropyl)-1,4-bis(phenylmethyl)piperazinone (XXI, Example 51) for 4-t-butoxycarbonyl-3-[2-(methylthio)ethyl]-1-(phenylmethyl)piperazinone there is obtained the title compound, m.p. 158°–161°.

EXAMPLE 53

3-Methyl-3-(2-methylpropyl)piperazinone (VIIB)

Following the general procedure of Example 40 and making non-critical variations, but substituting 3-methyl-3-(2-methylpropyl)-4-(phenylmethyl)piperazinone (XXII, Example 52) for 1,4-bis(phenylmethyl)piperazinone hydrochloride there is obtained the title compound, m.p. 79°–82°.

EXAMPLE 54

4-(2-Amino-1-oxo-3-phenylpropyl)-3-methyl-3-(2-methylpropyl)piperazinone (X)

Following the general procedure of Examples 57 and 58 and making non-critical variations, but substituting 3-methyl-3-(2-methylpropyl)piperazinone (VIIB) for 3,3-dimethylpiperazinone there is obtained the title compound.

EXAMPLE 55

3-Methyl-3-(2-methylpropyl)-4-(L-tyrosyl-D-alanylglycyl-D,L-phenylalanyl)piperazinone (XII)

Following the general procedure of Example 26 and making non-critical variations, but substituting 4-(2-amino-1-oxo-3-phenylpropyl)-3-methyl-3-(2-methylpropyl)piperazinone (X, Example 54) for hexahydro-3-[(S)-2-methylpropyl]-4-[(S)-2-amino-1-oxo-3-phenylpropyl]-2H-1,4-diazepin-2-one there is obtained the title compound as the trifluoroacetate salt.

EXAMPLE 56

3,3-Dimethylpiperazinone (VIIB)

Following the general procedure of Example 4 and making non-critical variations, but substituting ethyl α-bromoisobutyrate (V) for methyl-2-bromo-2-bromo-4-methylpeptanoate (V) there is obtained 3,3-dimethylpiperazinone.

EXAMPLE 57

4-[2-(1,3-dihydro-1,3-dioxo-2H-isoindol-2-yl)-1-oxo-3-phenylpropyl]-3,3-dimethylpiperazinone (XXIII)

2-(1,3-dihydro-1,3-dioxo-2H-isoindol-2-yl)-1-oxo-3-phenylpropionyl chloride (15.0 g.) is added to a stirred solution of 3,3-dimethyl-2-piperazinone (VIIB, Example 56, 15.0 g.) in DMF (100 ml.). After 2 hours the reaction is diluted with water and the precipitate is filtered off and air dried to give the title compound, m.p. 221°–223°.

EXAMPLE 58

4-(2-Amino-1-oxo-3-phenylpropyl)-3,3-dimethyl-piperazinone (X)

Hydrazine hydrate (2.0 g., 0.04 mole) is added to a stirred solution of 4-[2-(1,3-dihydro-1,3-dioxo-2H-isoindol-2-yl)-1-oxo-3-phenylpropyl]-3,3-dimethylpiperazinone (XXIII, Example 57, 10.0 g., 0.025 mole) in methanol (200 ml.). After refluxing for 2 hours the solution is cooled and filtered to remove the 2,3-dihydro-1,4-phthalazinedione by-product. The methanol is evaporated and the residual oil is recrystallized from water to give the title compound as the dihydrate, m.p. 70°–73°.

EXAMPLE 59

3,3-dimethyl-4-(L-tyrosyl-D-alanylglycyl-D,L-phenylalanyl)piperazinone (XII)

Following the general procedure of Example 26 and making non-critical variations, but substituting 4-(2-amino-1-oxo-3-phenylpropyl)-3,3-dimethylpiperazinone (X, Example 58) for hexahydro-4-[(S)-2-amino-1-oxo-3-phenylpropyl]-3-[(S)-2-methylpropyl]-2H-1,4-diazepin-2-one (X) there is obtained the title compound as the trifluoroacetate salt.

EXAMPLE 60

Ethyl bromo-(phenylmethyl)propanedioate XXVI)

A solution of potassium hydroxide (20.5 g.) in ethanol (240 ml.) is added to a stirred solution of diethyl benzylmalonate (XXIV, 90.3 g.) in ethanol (240 ml.). The reaction mixture is stirred at 20°–25° for 20 hours and the ethanol was removed, initially by evaporation under reduced pressure and then by lyophilization. The resulting solid (non-crystalline) is stirred in carbon tetrachloride (320 ml.) and cooled to 0°. A solution of bromine (60.0 g.) in carbon tetrachloride (160 ml.) is added dropwise to the stirred suspension. After 3 hours the solution is washed with water (3×50 ml.). Part of the carbon tetrachloride is removed and the precipitate is filtered off and washed with carbon tetrachloride, upon recrystallization from SSB, m.p. 95°–96°.

EXAMPLE 61

Ethyl 2-bromo-3-phenylpropionate (XXVII)

Ethyl bromo-(phenylmethyl)propandioate (XXVI, Example 60, 130 g.) is heated under reduced pressure to 140° with vigorous evolution of carbon dioxide. When decarboxylation is complete (about 5 minutes), the mixture is distilled to give ethyl 2-bromo-3-phenylpropionate, b.p. 120°/30 mm.

EXAMPLE 62

3-(Phenylmethyl)piperazinone (XXIX)

Ethylenediamine (25 g.) is added to a stirred solution of ethyl 2-bromo-3-phenylpropionate (XXVII, Example 61, 14.0 g.) in THF (100 ml.) and ethanol (300 ml.). After 20 hours at 20°–25° the solvents are removed under reduced pressure and the residual oil is partitioned between ethyl acetate-1N sodium hydroxide solution. The ethyl acetate extract is washed with water, saline, and concentrated. The residual oil is applied to a silica gel column which is eluted with chloroform-methanol (9/1). Fractions containing the product are pooled, concentrated to a residue and recrystallized from ethyl acetate-SSB to give 3-(phenylmethyl)-piperazinone, m.p. 92°–93°.

EXAMPLE 63

Benzyl-3-oxo-2-(phenylmethyl)-1-piperazinecarboxylate (XXX)

Benzyl chloroformate (8.5 g.) is added to a stirred mixture of 3-(phenylmethyl)piperazinone (XXIX, Example 62, 6.8 g.), chloroform (75 ml.), and saturated sodium bicarbonate solution (20 ml.). After 30 minutes the chloroform phase is separated, washed twice with water, and concentrated. The residual oil is crystallized from ethyl acetate-SSB and then ethyl acetate again to give the title compound, m.p. 125°–127.5°.

EXAMPLE 64

Methyl α-(2-methylpropyl)-2-oxo-4-[(phenylmethoxy)carbonyl]-3(phenylmethyl)-1-piperazine acetate (XXXI, isomer A is a L,L-; D,D-mixture and isomer B is a L,D-; D,L- mixture)

Sodium hydride (1.75 g., 50% in oil) is added to a stirred solution of benzyl 3-oxo-2-(phenylmethyl)-1-piperazinecarboxylate (XXX, Example 63, 10.8 g.) in THF (200 ml.). The mixture is stirred for 15 minutes at which time methyl 2-bromo-4-methylpentanoate (10 g.) is added and stirring is continued for 3 hours. The THF is removed under reduced pressure and the residue is dissolved in ethyl acetate (400 ml.) and methanol (10 ml.). The solution is washed with water (3×100 ml.) and saline. Removal of the ethyl acetate gave an oil which is column chromatographed on silica gel. Elution with diethyl ether-SSB (1/1) gives, as the first product eluted from the column "isomer A", a mixture of the L,L- and D,D-isomers, methyl α-[(S)-2-methylpropyl]-2-oxo-4-(phenylmethoxycarbonyl)-3-[(S)-phenylmethyl]-1-piperazine acetate and methyl α-[(R)-2-methylpropyl]-2-oxo-4-(phenylmethoxycarbonyl)-3-[(R)-phenylmethyl]-1-piperazine acetate, which upon crystallization (2×) from ethyl acetate-SSB has a m.p. of 51°–54°.

Continued elution of the column gives "isomer B", a mixture of L,D- and D,L-isomers, methyl α-[(S)-2-methylpropyl]-2-oxo-4-(phenylmethoxycarbonyl)-3-[(R)-phenylmethyl]-1-piperazine acetate and methyl α-[(R)-2-methylpropyl]-2-oxo-4-(phenylmethoxycarbonyl)-3-[(S)-phenylmethyl]-1-piperazine acetate, pure material is obtained by recrystallization from ethyl acetate and then from methanol to give m.p. 65°–70°.

EXAMPLE 65

α[(S)-2-methylpropyl]-2-oxo-4-[(phenylmethoxy)carbonyl]-3-[(S)-phenylmethyl]-1-piperazineacetamide and α-[(R)-2-methylpropyl]-2-oxo-4-[(phenylmethoxy)carbonyl]-3-[(R)-phenylmethyl]-1-piperazineacetamide (XXXII)

A solution of the (S)(S) and (R)(R) isomers (XXXI, Example 64) in ammonia/methanol (20/80, 50 ml.) is left at 20°–25° for 7 days. The methanol is then removed and the residual solid is crystallized from ethyl acetate-SSB and recrystallized from ethyl acetate to give the title compound, m.p. 122°–124°.

EXAMPLE 66

α-[(S)-2-Methylpropyl]-2-oxo-3-[(S)-phenylmethyl]-1-piperazineacetamide and α-[(R)-2-methylpropyl]-2-oxo-3-[(R)-phenylmethyl]-1-piperazineacetamide (XXXIII)

A mixture of the (S)(S) and (R)(R) isomers (XXXII, Example 65) 10% palladium charcoal (0.5 g.) and methanol (200 L ml.) is hydrogenated (50 lb. initial hydrogen pressure) for 30 minutes. The solution was filtered and the catalyst is washed with methanol. Evaporation of the methanol gives an oil which is partitioned between chloroform (150 ml.) and sodium hydroxide (1N, 10 ml.). The chloroform solution is washed twice with water, dried and the chloroform is removed under reduced pressure to give an oil which is crystallized from ethyl acetate-SSB and recrystallized from ethyl acetate-SSB to give the title compound, m.p. 108°–110°.

EXAMPLE 67

α-[(S)-2-methylpropyl]-2-oxo-3-[(R)-phenylmethyl]-1-piperazineacetamide and α-[(R)-2-methylpropyl]-2-oxo-3-[(S)-phenylmethyl]-1-piperazineacetamide (XXXIII)

Following the general procedure of Examples 65 and 66 and making non-critical variations but starting with the (R)(S) and (S)(R) isomers (XXXI, Example 64) the title compound is obtained and upon recrystallization from ethyl acetate, m.p. 142°–144°.

EXAMPLE 68

α-[(S)-2-methylpropyl]-2-oxo-3-[(S)-phenylmethyl]-4-(L-tyrosyl-D-alanylglycyl)-1-piperazineacetamide and α-[(R)-2-methylpropyl]-2-oxo-3-[(R)-phenylmethyl]-4-(L-tyrosyl-D-alanylglycyl)-1-piperazinoneacetamide Following the general procedure of Example 19 and making non-critical variations, but substituting a mixture of α-[(S)-2-methylpropyl]-2-oxo-3-[(S)-phenylmethyl]-1-piperazineacetamide and α-[(R)-2-methylpropyl]-2-oxo-3-[(R)-phenylmethyl]-1-piperazineacetamide (XXXIII, Example 66) for 3-(2-methylpropyl)-piperazinone there is obtained the title compound as a mixture of the acetate and fluoride salts.

EXAMPLE 69

4-[N-carbobenzyloxyglycyldehydrophenylalanyl]-3-(2-methylpropyl)piperazinone (XXXVI)

3-(2-methylpropyl)piperazinone (VII, Example 4, 1.5 g.) is added to a solution of N-carbobenzoxyglycyl-dehydrophenylalanine azlactone [XXXV, 1.0 g., Biochem. & Biophy. Res. Comm. 85, 780 (1978)] in ethyl acetate. The solution is refluxed for 24 hours and the product is chromatographed on silica gel to give the title compound.

EXAMPLE 70

4-(Glycyldehydrophenylalanyl)-3-(2-methylpropyl)-piperazinone (XXXVII)

4-[N-carbobenzyloxyglycyldehydrophenylalanyl]-3-(2-methylpropyl)piperazinone (XXXVI, Example 69, 0.5 g.) is added to a solution of hydrogen bromide (32%) in acetic acid (5 ml.). After 1 hour the diluents are evaporated to give the title compound as the hydrobromide salt.

EXAMPLE 71

3-(2-methylpropyl-4-(L-tyrosyl-D-alanylglycyldehydrophenylalanyl)piperazinone (XXXIX)

Following the general procedure of Example 26 and making non-critical variations, but substituting t-butoxycarbonyl-L-tyrosyl-D-alanine (XXXVIII) for t-butoxycarbonyl-L-tyrosyl-D-alanylglycine and 3-(2-methylpropyl)-4-glycyldehydrophenylalanyl)piperazinone (XXXVII, Example 70) for 3-(2-methylpropyl)piperazinone there is obtained the title compound as the trifluoroacetate salt.

EXAMPLE 72

3-(2-Methylpropyl)-4-(phenylmethyl)piperazinone (XL)

Following the general procedure of Example 43 and making non-critical variations, but substituting 3-(2-methylpropyl)-1,4-bis(phenylmethyl)piperazinone (XVIII, Example 50) for 4-t-butoxycarbonyl-3-[2-(methylthio)ethyl]-1-(phenylmethyl)piperazinone there is obtained the title compound, m.p. 126°–127°.

EXAMPLE 73

2-(2-Methylpropyl)-1-(phenylmethyl)piperazine (XLI)

Lithium aluminum hydride (3.56 g., 0.094 mole) is added to a stirred solution of 3-(2-methylpropyl)-4-(phenylmethyl)piperazinone (XL, Example 72, 17.43 g., 0.075 mole) in THF (720 ml.). The solution is refluxed for 5 hours and is then cooled. Ethyl acetate is added and the product is partitioned between ether and water. The ether is removed and the product is distilled to give the title compound, a b.p. of 98° at 0.05 mm pressure.

EXAMPLE 74

4-t-butoxycarbonyl-2-(2-methylpropyl)-1-(phenylmethyl)piperazine, p-toluenesulfonate salt (XLII)

A mixture of 2-(2-methylpropyl)-1-(phenylmethyl)-piperazine (XLI, Example 73, 14.0 g., 0.06 mole) and 2-t-(butoxycarbonyloxyimino)-2-phenylacetonitrile in benzene (100 ml.) is heated under reflux for 1.5 hour. The benzene is removed under reduced pressure and the product is chromotographed on silica gel to give the title compound which is converted to the p-TSA, m.p. 146°–148° (dec.).

EXAMPLE 75

1-t-Butoxycarbonyl-3-(2-methylpropyl)piperazine, p-toluene sulfonate salt (XLIII)

Following the general procedure of Example 48 and making non-critical variations, but substituting 4-t-butoxycarbonyl-2-(2-methylpropyl)-1-(phenylmethyl)-piperazine (XLII, Example 74) for 1-methyl-3-(2-methylpropyl)-4-(phenylmethyl)piperazine there is obtained the title compound, m.p. 132°–138°.

EXAMPLE 76

4-[(S)-2-amino-1-oxo-3-phenylpropyl]-1-t-butoxycarbonyl-3-[(S)-2-methylpropyl]piperazine and 4[(S)-2-amino-1-oxo-3-phenylpropyl]-1-t-butoxycarbonyl-3-[(R)-2-methylpropyl]piperazine (XLIV)

Following the general procedure of Example 8 and making non-critical variations, but substituting 1-t-butoxycarbonyl-3-(2-methylpropyl)piperazine (XLIII, Example 75) for 3-(2-methylpropyl)piperazinone there is obtained 4-[(S)-2-amino-1-oxo-3-phenylpropyl]-1-t-butoxycarbonyl-3-[(S)-2-methylpropyl]piperazine, m.p. 122°–124°; and 4-[(S)-2-amino-1-oxo-3-phenylpropyl]-1-t-butoxycarbonyl-3-[(R)-2-methylpropyl]piperazine, m.p. 90°–95°.

EXAMPLE 77

4-[(S)-Methylamino-1-oxo-3-phenylpropyl]-1-t-butoxycarbonyl-3-[(S)-2-methylpropyl]piperazine and 4-[(S)-Methylamino-1-oxo-3-phenylpropyl-1-t-butoxycarbonyl-3-[(R)-2-methylpropyl]piperazine (XLIV)

Following the general procedure of Example 15 and making non-critical variations, but substituting 1-t-butoxycarbonyl-3-(2-methylpropyl)piperazine (XLIII, Example 75) for 3-(2-methylpropyl)piperazinone there is obtained 4-[(S)-2-methylamino-1-oxo-3-phenylpropyl]-1-t-butoxycarbonyl-3-[(S)-2-methylpropyl]piperazine and 4-[(S)-2-methylamino-1-oxo-3-phenylpropyl]-1-t-butoxycarbonyl-3-[(S)-2-methylpropyl]piperazine.

EXAMPLE 78

2-[(S)-2-Methylpropyl]-1-(L-tyrosyl-D-alanylglycyl-L-phenylalanyl)piperazine (XLV)

Following the general procedure of Example 26 and making non-critical variations, but substituting 4-[(S)-2-amino-1-oxo-3-phenylpropyl]-1-t-butoxycarbonyl-3-[(S)-2-methylpropyl]piperazine (XLIV, Example 76) for hexahydro-4-[(S)-2-amino-1-oxo-3-phenylpropyl]-3-[(S)-2-methylpropyl]-2H-1,4-diazepin-2-one there is obtained the title compound as the bis trifluoroacetate salt.

EXAMPLE 79

2-[(R)-2-methylpropyl]-1-(L-tyrosyl-D-alanylglycyl-L-phenylalanyl)piperazine (XLV)

Following the general procedure of Example 26 and making non-critical variations, but substituting 4-[(S)-2-amino-1-oxo-3-phenylpropyl]-1-t-butoxycarbonyl-3-[(R)-2-methylpropyl]piperazine (XLIV, Example 76) for hexahydro-4-[(S)-2-amino-1-oxo-3-phenylpropyl]-3-[(S)-2-methylpropyl]-2H-1,4-diazepin-2-one there is obtained the title compound as the bis trifluoroacetate salt.

EXAMPLE 80

2-[(S)-2-methylpropyl]-1-(L-tyrosyl-D-alanylglycyl-L-N-methylphenlalanyl)piperazine (XLV)

Following the general procedure of Example 26 and making non-critical variations, but substituting 4-[(S)-methylamino-1-oxo-3-phenylpropyl]-1-t-butoxycarbonyl-3-[(S)-2-methylpropyl]piperazine (XLIV, Example 77) for hexahydro-4-[(S)-2-amino-1-oxo-3-phenylpropyl]-3-[(S)-2-methylpropyl]-2H-1,4-diazepin-2-one there is obtained the title compound as the bis trifluoroacetate salt.

EXAMPLE 81

2-[(R)-2-methylpropyl]-1-(L-tyrosyl-D-alanylglycyl-L-N-methylphenylalanyl)piperazine (XLV)

Following the general procedure of Example 26 and making non-critical variations, but substituting 1-t-butoxycarbonyl-4-[(S)-2-methylamino-1-oxo-3-phenyl-propyl]-3-[(R)-methylpropyl]piperazine for hexahydro-4-[(S)-2-amino-1-oxo-3-phenylpropyl]-3-[(S)-2-methyl-propyl]-2H-1,4-diazepin-2-one there is obtained the title compound as the bis trifluoroacetate salt.

EXAMPLE 82

4-[(S)-2-methylamino-1-oxo-3-phenylpropyl]-3-[(S)-2-(methylthio)ethyl]piperazinone and 4-[(S)-2-methylamino-1-oxo-3-phenylpropyl]-3-[(R)-2-(methylthio)ethyl]piperazinone (X)

Following the general procedure of Example 15 and making non-critical variations, but substituting 3-[2-(methylthio)ethyl]piperazinone (VII) for 3-(2-methyl-propyl)piperazinone there is obtained the title compound.

EXAMPLE 83

5,5-Dimethyl-3-(2-methylpropyl)piperazinone (VII)

A mixture of 4-methylpentanoic acid (46.4 g., 0.4 mole) and thionyl chloride (59.5 g., 0.5 mole) is heated under reflux for 2 hours. The solution is cooled, bromine (63.9 g., 0.4 mole) is added, and the reaction mixture is refluxed for 3 hours. Distillation under reduced pressure gives 2-bromo-4-methylpentanoyl chloride (IV) having a boiling point of 100° at 30 mm pressure. A portion (21.6 g., 0.1 mole) of this product is added dropwise at $-10°$ to a stirred mixture of 1,2-diamino-2-methylpropane (17.6 g., 0.2 mole) anhydrous sodium carbonate (20.0 g., 0.19 mole) in methanol (200 ml.). The solution is allowed to warm to 20°–25° and is then refluxed for 18 hours. The methanol is removed under reduced pressure and the mixture is partitioned between chloroform (250 ml.) and 5N sodium hydroxide solution 940 ml.). The chloroform phase is washed with water ($2 \times 20$ ml.), the chloroform is evaporated and the residual oil is crystallized from ethyl acetate:SSB to give the title compound, m.p. 112°–115°.

EXAMPLE 84

4-(2-amino-1-oxo-3-phenylpropyl)-5,5-dimethyl-3-(2-methylpropyl)piperazinone (X)

Following the general procedure of Examples 57 and 58 and making non-critical variations, but substituting 5,5-dimethyl-3-(2-methylpropyl)piperazinone (VII, Example 83) for 3,3-dimethylpiperazinone there is obtained the title compound.

EXAMPLE 85

4-(2-amino-1-oxo-3-phenylpropyl)-5,5-dimethyl-piperazinone (X)

Following the general procedure of Examples 57 and 58 and making non-critical variations, but substituting 5,5-dimethylpiperazinone (VII) for 3,3-dimethyl-piperazinone there is obtained the title compound.

I claim:

1. A compound selected from the group consisting of compounds of the formula

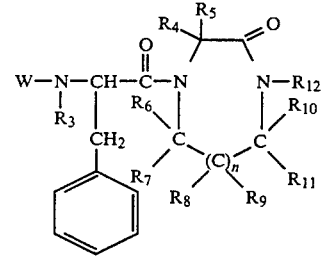 (IX)

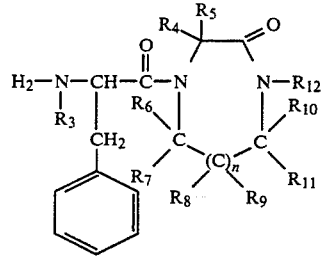 (X)

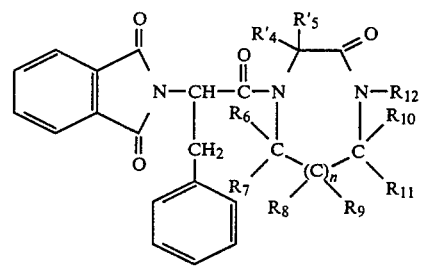 (XXIII)

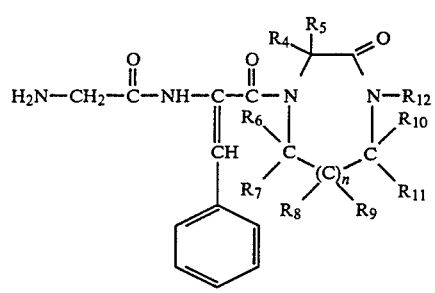 (XXXVII)

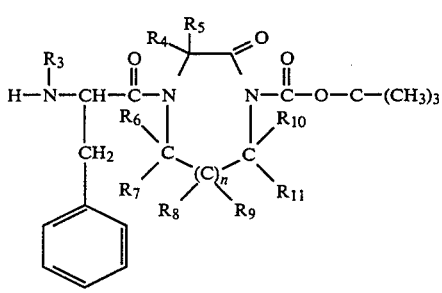 (XLIV)

and salts thereof where
$R_3$ is a hydrogen atom or methyl group;
$R_4$ is a hydrogen atom, alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms;
$R_{4a}$ is alkyl of 1 thru 3 carbon atoms;
$R_{4b}$ is alkyl of 1 thru 3 carbon atoms;

43

$R_4'$ is alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms;

$R_5$, $R_6$, $R_7$, $R_8$, $R_9$, $R_{10}$, $R_{11}$, $R_{12}$ are when present independently a hydrogen atom, alkyl of 1 thru 4 carbon atoms, cycloalkyl of 3 thru 5 carbon atoms, cycloalkyl substituted alkyl of 4 thru 7 carbon atoms total with the proviso that the total number of carbon atoms in all these groups together when present is 0 thru 10;

$R_5'$ is alkyl of 1 thru 4 carbon atoms, cycloalkyl of 3 thru 5 carbon atoms, cycloalkyl substituted alkyl of 4 thru 7 carbon atoms total with the proviso that the total number of carbon atoms of $R_5'$ and $R_6$-$R_{12}$ together when present is 1 thru 10;

n is 0 or 1; and

W is an amino blocking group selected from the group consisting of benzyloxycarbonyl or t-butoxycarbonyl.

2. A compound according to claim 1 where $R_3$ is a hydrogen atom.

3. A compound according to claim 1 where $R_3$ is a methyl group.

4. A compound according to claim 1 where $R_4$ is iso-butyl or $CH_3$—S—$CH_2CH_2$—.

5. A compound according to claim 1 where $R_5$, $R_6$, $R_7$, $R_8$, $R_9$, $R_{10}$, $R_{11}$, and $R_{12}$ are a hydrogen atom or methyl group.

6. A compound according to claim 1 where $R_5$, $R_6$, $R_7$, $R_8$, $R_9$, $R_{10}$, $R_{11}$, and $R_{12}$ are a hydrogen atom.

7. A compound according to claim 1 where n is zero.

8. A compound according to claim 1 of formula (X) which is selected from the group consisting of 4-[(S)-2-amino-1-oxo-3-phenylpropyl)-3-[(S)-2-methylpropyl]-piperazinone, 4-[(S)-2-amino-1-oxo-3-phenylpropyl)-3-[(R)-2-methylpropyl]piperazinone, 4-(2-amino-1-oxo-3-phenylpropyl)-5,5-dimethylpiperazinone, 4-[(S)-2-amino-1-oxo-3-phenylpropyl]piperazinone, 4-[(S)-2-amino-1-oxo-3-phenylpropyl]-3-[(S)-methyl]-piperazinone, 4-[(S)-2-amino-1-oxo-3-phenylpropyl]-3-[(R)-methyl]-piperazinone, 4-[(S)-2-amino-1-oxo-3-phenylpropyl]-1-methyl-3-[(S)-2-methylpropyl]piperazinone, 4-[(S)-2-amino-1-oxo-3-phenylpropyl]-1-methyl-3-[(R)-2-methylpropyl]piperazinone, hexahydro-4-[(S)-2-amino-1-oxo-3-phenylpropyl]-3-[(S)-2-methylpropyl]-2H-1,4-diazepin-2-one, hexahydro-4-[(S)-2-amino-1-oxo-3-phenylpropyl]-3-[(R)-2-methylpropyl]-2H-1,4-diazepin-2-one, 4-[(S)-2-amino-1-oxo-3-phenylpropyl)-6,6-dimethyl-3-[(S)-2-methylpropyl]piperazinone, 4-[(S)-2-amino-1-oxo-3-phenylpropyl]-6,6-dimethyl-3-[(R)-2-methylpropyl]piperazinone, 4-[(S)-2-methylamino-1-oxo-3-phenylpropyl]-3-[(S)-2-methylpropyl]piperazinone, 4-[(S)-2-methylamino-1-oxo-3-phenylpropyl]-3-[(R)-2-methylpropyl]piperazinone, 4-[(S)-2-amino-1-oxo-3-phenylpropyl]-3-[(S)-2-(methylthio)ethyl]piperazinone, 4-[(S)-2-amino-1-oxo-3-phenylpropyl]-3-[(R)-2-methylthio)ethyl]piperazinone, 4-[(S)-2-amino-1-oxo-3-phenylpropyl]-6,6-dimethylpiperazinone, 4-(2-amino-1-oxo-3-phenylpropyl)-3,3-dimethylpiperazinone, 4-[(S)-2-methylamino-1-oxo-3-phenylpropyl]-3-[(S)-2-(methylthio)ethyl]piperazinone, 4-[(S)-2-methylamino-1-oxo-3-phenylpropyl]-3-[(R)-2-methylthio)ethyl]piperazinone, 4-(2-amino-1-oxo-3-phenylpropyl)-5,5-dimethyl-3-(2-methylpropyl)piperazinone.

44

9. A compound according to claim 1 of formula (XXIII) which is 4-[2-(1,3-dihydro-1,3-dioxo-2H-isoindol-2-yl)-1-oxo-3-phenylpropyl]-3,3-dimethyl-2-piperazinone.

10. A compound according to claim 1 of formula (XXXVII) which is 4-(glycyldehydrophenylalanyl)-3-(2-methylpropyl)-piperazinone.

11. A compound according to claim 1 of formula (XLIV) which is selected from the group consisting of 4-[(S)-2-amino-1-oxo-3-phenylpropyl]-1-t-butoxycarbonyl-3-[(S)-2-methylpropyl]piperazine, 4-[(S)-2-amino-1-oxo-3-phenylpropyl]-1-t-butoxycarbonyl-3-[(R)-2-methylpropyl]piperazine, 4-[(S)-methylamino-1-oxo-3-phenylpropyl]-1-t-butoxycarbonyl-3-[(S)-2-methylpropyl]piperazine, 4-[(S)-methylamino-1-oxo-3-phenylpropyl-1-t-butoxycarbonyl-3-[(R)-2-methylpropyl]piperazine.

12. A compound selected from the group consisting of compounds of the formula $$\begin{array}{c} R_4'_4 \quad\quad O \\ \diagdown\diagup \\ W'-N \quad\quad N-H \\ R_6\diagdown | \quad\quad |\diagup R_{10} \\ C \quad\quad C \\ \diagup \diagdown (C)_n \diagdown R_{11} \\ R_7 \quad R_8 \quad R_9 \end{array}$$ (XVII)

$$\begin{array}{c} R_4' \quad R_5'5 \; O \\ \diagdown\diagup \\ W'-N \quad\quad N-H \\ R_6\diagdown | \quad\quad |\diagup R_{10} \\ C \quad\quad C \\ \diagup \diagdown (C)_n \diagdown R_{11} \\ R_7 \quad R_8 \quad R_9 \end{array}$$ (XXII)

and salts thereof where $R_4'$ is alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms;

$R_{4a}$ is alkyl of 1 thru 3 carbon atoms;

$R_{4b}$ is alkyl of 1 thru 3 carbon atoms;

$R_5'$ is alkyl of 1 thru 4 carbon atoms, cycloalkyl of 3 thru 5 carbon atoms, cycloalkyl substituted alkyl of 4 thru 7 carbon atoms total with the proviso that the total number of carbon atoms of $R_5'$ and $R_6$-$R_{12}$ together when present is 1 thru 10;

$R_6$, $R_7$, $R_8$, $R_9$, $R_{10}$, $R_{11}$, $R_{12}$ are when present independently a hydrogen atom, alkyl of 1 thru 4 carbon atoms, cycloalkyl of 3 thru 5 carbon atoms, cycloalkyl substituted alkyl of 4 thru 7 carbon atoms total with the proviso that the total number of carbon atoms in all these groups together when present is 0 thru 10;

n is 0 or 1; and

W is an amino blocking group selected from the group consisting of benzyloxycarbonyl or t-butoxycarbonyl.

13. A compound according to claim 12 where $R_4$ is isobutyl or $CH_3$—S—$CH_2CH_2$—.

14. A compound according to claim 12 where $R_6$, $R_7$, $R_8$, $R_9$, $R_{10}$, $R_{11}$, and $R_{12}$ are a hydrogen atom or methyl group.

15. A compound according to claim 12 where $R_5$, $R_6$, $R_7$, $R_8$, $R_9$, $R_{10}$, $R_{11}$, and $R_{12}$ are a hydrogen atom.

16. A compound according to claim 12 where n is zero.

17. A compound according to claim 12 of formula (XVII) which is 4-t-butoxycarbonyl-3-[2-(methylthio)ethyl]piperazinone.

18. A compound according to claim 12 of formula (XXII) which is 3-methyl-3-(2-methylpropyl)-4-(phenylmethyl)piperazinone.

19. A compound selected from the group consisting of compounds of the formula

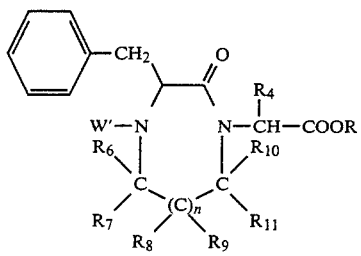

(XXXI)

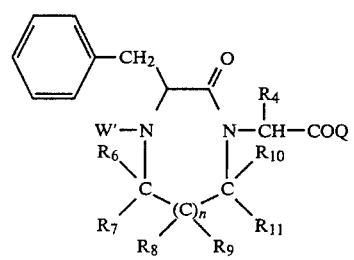

(XXXII)

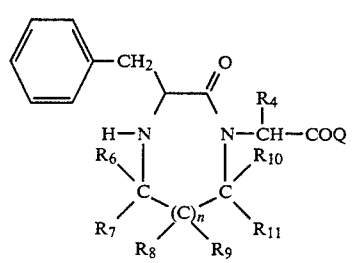

(XXXIII)

and salts thereof where
R is a primary or secondary alkyl group of 1 thru 6 carbon atoms, cyclohexyl or phenyl;
$R_4$ is a hydrogen atom, alkyl of 1 thru 6 carbon atoms, cycloalkyl substituted alkyl of 4 thru 7 carbon atoms total, hydroxyalkyl where the alkyl portion is 1 thru 4 carbon atoms, $R_{4a}$—S—$R_{4b}$— or amino substituted alkyl where the alkyl portion is 2 thru 5 carbon atoms;
$R_{4a}$ is alkyl of 1 thru 3 carbon atoms;
$R_{4b}$ is alkyl of 1 thru 3 carbon atoms;
$R_6$, $R_7$, $R_8$, $R_9$, $R_{10}$, $R_{11}$ are when present independently a hydrogen atom, alkyl of 1 thru 4 carbon atoms, cycloalkyl of 3 thru 5 carbon atoms, cycloalkyl substituted alkyl of 4 thru 7 carbon atoms total with the proviso that the total number of carbon atoms in all these groups together when present is 0 thru 10;
n is 0 or 1; and
W' is W or benzyl;
W is an amino blocking group selected from the group consisting of benzyloxycarbonyl or t-butoxycarbonyl;
Q is hydroxyl, alkoxy where the alkyl group is 1 thru 3 carbon atoms, amino, $R_{13a}$—N—$R_{13b}$, cycloalkyl substituted alkylamino where the cycloalkyl substituted alkyl portion is 4 thru 7 carbon atoms;
$R_{13a}$ is a hydrogen atom or alkyl of 1 thru 4 carbon atoms;
$R_{13b}$ is alkyl of 1 thru 4 carbon atoms.

20. A compound according to claim 19 where $R_4$ is iso-butyl or $CH_3$—S—$CH_2CH_2$—.

21. A compound according to claim 19 where $R_6$, $R_7$, $R_8$, $R_9$, $R_{10}$, $R_{11}$, and $R_{12}$ are a hydrogen atom or methyl group.

22. A compound according to claim 19 where $R_6$, $R_7$, $R_8$, $R_9$, $R_{10}$, $R_{11}$, and $R_{12}$ are a hydrogen atom.

23. A compound according to claim 19 where n is zero.

24. A compound according to claim 19 where R is a methyl group.

25. A compound according to claim 19 where Q is amino.

26. A compound according to claim 19 of formula (XXXI) which is methyl-α-(2-methylpropyl)-2-oxo-4-[(phenylmethoxy)carbonyl]-3-(phenylmethyl)-1-piperazineacetate.

27. A compound according to claim 19 of formula (XXXII) which is α-(2-methylpropyl)-2-oxo-4-[(phenylmethoxy)carbonyl]-3-(phenylmethyl)-1-piperazineacetamide.

28. A compound according to claim 19 of the formula (XXXIII) which is selected from the group consisting of α-[(S)-2-methylpropyl]-2-oxo-3-[(S)-phenylmethyl]-1-piperazineacetamide, α-[(R)-2-methylpropyl]-2-oxo-3-[(R)-phenylmethyl]-1-piperazineacetamide, α-[(S)-2-methylpropyl]-2-oxo-3-[(R)-phenylmethyl]-1-piperazineacetamide, α-[(R)-2-methylpropyl]-2-oxo-3-[(S)-phenylmethyl]-1-piperazineacetamide.

29. A compound selected from the group consisting of 3-(2-methylpropyl)piperazinone, hexahydro-3-(2-methylpropyl)-2H-1,4-diazepin-2-one, 6,6-dimethyl-3-(2-methylpropyl)piperazinone, 5,5-dimethylpiperazinone, 3-[2-methylthio)ethyl]piperazinone, 3-methyl-3-(2-methylpropyl)piperazinone, 5,5-dimethyl-3-(2-methylpropyl)piperazinone, 3-(2-methylpropyl-1,4-bis(phenylmethyl)piperazinone, hydrochloride, 1-(phenylmethyl)piperazinone hydrochloride, 4-(t-butoxycarbonyl)-1-(phenylmethyl)piperazinone, 1-methyl-4-(phenylmethyl)piperazinone, 1-methyl-3-(2-methylpropyl)-4-(phenylmethyl)piperazinone, 1-methyl-3-(2-methylpropyl)piperazinone, 3-methyl-1,4-bis(phenylmethyl)piperazinone hydrochloride, 3-methyl-3-(2-methylpropyl)-1,4-bis(phenylmethyl)piperazinone, 3-(phenylmethyl)piperazinone, benzyl-3-oxo-2-(phenylmethyl)-1-piperazinecarboxylate, 3-(2-methylpropyl)-4-(phenylmethyl)piperazinone, 2-(2-methylpropyl)-1-(phenylmethyl)piperazine, 4-t-butoxycarbonyl-2-(2-methylpropyl)-1-(phenylmethyl)piperazine, 1-t-butoxycarbonyl-3-(2-methylpropyl)piperazine and salts thereof.

30. A compound selected from the group consisting of compounds of the formula

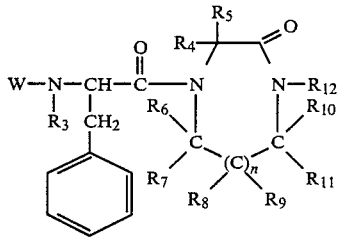

(IX)

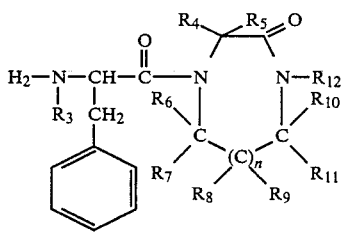

(X)

and salts thereof where

R$_3$ is a hydrogen atom or methyl group;

R$_4$ is a hydrogen atom, alkyl of 1 thru 6 carbon atoms, cycloalkyl substituted alkyl of 4 thru 7 carbon atoms total, hydroxyalkyl where the alkyl portion is 1 thru 4 carbon atoms, R$_{4a}$—S—R$_{4b}$— or amino substituted alkyl where the alkyl portion is 2 thru 5 carbon atoms;

R$_{4a}$ is alkyl of 1 thru 3 carbon atoms;

R$_{4b}$ is alkyl of 1 thru 3 carbon atoms;

R$_5$, R$_6$, R$_7$, R$_8$, R$_9$, R$_{10}$, R$_{11}$, R$_{12}$ are when present independently a hydrogen atom, alkyl of 1 thru 4 carbon atoms, cycloalkyl of 3 thru 5 carbon atoms, cycloalkyl substituted alkyl of 4 thru 7 carbon atoms total with the proviso that the total number of carbon atoms in all these groups together when present is 0 thru 10;

n is 0 or 1; and

W is an amino blocking group selected from the group consisting of benzyloxycarbonyl or t-butoxycarbonyl.

31. A compound according to claim 30 where R$_3$ is a hydrogen atom.

32. A compound according to claim 30 where R$_3$ is a methyl group.

33. A compound according to claim 30 where R$_4$ is iso-butyl or CH$_3$—S—CH$_2$CH$_2$—.

34. A compound according to claim 30 where R$_5$, R$_6$, R$_7$, R$_8$, R$_9$, R$_{10}$, R$_{11}$ and R$_{12}$ are a hydrogen atom or methyl group.

35. A compound according to claim 30 where R$_5$, R$_6$, R$_7$, R$_8$, R$_9$, R$_{10}$, R$_{11}$ and R$_{12}$ are a hydrogen atom.

36. A compound according to claim 30 where n is zero.

* * * * *